United States Patent
Kim et al.

(10) Patent No.: US 10,017,570 B2
(45) Date of Patent: Jul. 10, 2018

(54) REPEBODY FOR NOVEL INTERLEUKIN-6 AND USE THEREOF

(71) Applicants: KOREA ADVANCED INSTITUTE OF SCIENCE AND TECHNOLOGY, Daejeon (KR); THE INDUSTRY & ACADEMIC COOPERATION IN CHUNGNAM NATIONAL UNIVERSITY (IAC), Daejeon (KR); KOREA BASIC SCIENCE INSTITUTE, Daejeon (KR)

(72) Inventors: Hak-Sung Kim, Daejeon (KR); Joong-Jae Lee, Daejeon (KR); Jung Min Choi, Daejeon (KR); Eun-Kyeong Jo, Daejeon (KR); Chul-Su Yang, Daejeon (KR); Hae-Kap Cheong, Chungcheongbuk-do (KR); Hyun Jung Kim, Chungcheongbuk-do (KR)

(73) Assignees: KOREA ADVANCED INSTITUTE OF SCIENCE AND TECHNOLOGY, Daejeon (KR); THE INDUSTRY & ACADEMIC COOPERATION IN CHUNGNAM NATIONAL UNIVERSITY (IAC), Daejeon (KR); KOREA BASIC SCIENCE INSTITUTE, Daejeon (KR)

( * ) Notice: Subject to any disclaimer, the term of this patent is extended or adjusted under 35 U.S.C. 154(b) by 339 days.

(21) Appl. No.: 14/381,407

(22) PCT Filed: Feb. 27, 2013

(86) PCT No.: PCT/KR2013/001605
§ 371 (c)(1),
(2) Date: Oct. 7, 2014

(87) PCT Pub. No.: WO2013/129852
PCT Pub. Date: Sep. 6, 2013

(65) Prior Publication Data
US 2015/0094450 A1    Apr. 2, 2015

(30) Foreign Application Priority Data

Feb. 27, 2012  (KR) .................. 10-2012-0019927
Jan. 23, 2013  (KR) .................. 10-2013-0007380

(51) Int. Cl.
C07K 16/24    (2006.01)
C07K 14/705    (2006.01)
C07K 14/195    (2006.01)
C07K 14/54    (2006.01)
C07K 14/725    (2006.01)

(52) U.S. Cl.
CPC ........ *C07K 16/248* (2013.01); *C07K 14/195* (2013.01); *C07K 14/5412* (2013.01); *C07K 14/705* (2013.01); *C07K 14/7051* (2013.01); *C07K 2318/00* (2013.01); *C07K 2319/00* (2013.01); *C07K 2319/70* (2013.01); *C07K 2319/73* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1

FOREIGN PATENT DOCUMENTS

KR    10-2011-0099600 A    9/2011
KR    10-2013-0098089 A    9/2013

OTHER PUBLICATIONS

Pancer et al (Nature. Jul. 8, 2004;430(6996):174-80).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Bonovas et al (Anticancer Research. 28: 1857-1866 (2008)).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Kim, H., et al., "IS1-2: Design of a Binding Scaffold Based on Repeat Proteins by Module Engineering", "2011 International Symposium and Annual Meeting Translational Research in Microbiology and Biotechnology", Jun. 22, 2011, pp. 88 Published in: Gyeongju, Republic of Korea.
Lee, S., et al., "Design of a binding scaffold based on variable lymphocyte receptors of jawless vertebrates by module engineering", "PNAS", Feb. 28, 2012, pp. 3299-3304, vol. 109, No. 9.

(Continued)

*Primary Examiner* — Brian Gangle
*Assistant Examiner* — Andrea K McCollum
(74) *Attorney, Agent, or Firm* — Hultquist, PLLC; Steven J. Hultquist

(57) ABSTRACT

The present invention relates to an repebody capable of binding specifically to interleukin-6 (IL-6) to inhibit the biological activity of IL-6, a polynucleotide encoding the repebody, a vector comprising the polynucleotide, a recombinant microorganism having introduced therein the polynucleotide or the vector, a method of producing the repebody using the recombinant microorganism, a composition for preventing or treating cancer, which comprises the repebody, and a method for preventing or treating cancer, which comprises administering the composition for preventing or treating cancer, which comprises the repebody. The repebody of the present invention significantly reduces the activity of signal transduction and activator of transciption3 (STAT3) and the concentration of interleukin-6, and thus can be widely used as an agent for preventing or treating IL-6-related diseases.

7 Claims, 10 Drawing Sheets

(56) References Cited

OTHER PUBLICATIONS

Wezner-Ptasinska, M., et al., "Design and characteristics of a stable protein scaffold for specific binding based on variable lymphocyte receptor sequences", "Biochimica et Biophysica Acta", May 18, 2011, pp. 1140-1145, vol. 1814.

Alder, M., et al., "Diversity and Function of Adaptive Immune Receptors in a Jawless Vertebrate", "Science", Dec. 23, 2005, pp. 1970-1973, vol. 310.

* cited by examiner

REPEBODY FOR NOVEL INTERLEUKIN-6 AND USE THEREOF

CROSS-REFERENCE TO RELATED APPLICATIONS

This application is a U.S. national phase under the provisions of 35 U.S.C. § 371 of International Patent Application No. PCT/KR13/01605 filed Feb. 27, 2013, which in turn claims priority of Korean Patent Application No. 10-2012-0019927 filed Feb. 27, 2012 and Korean Patent Application No. 10-2013-0007380 filed Jan. 23, 2013. The disclosures of such international patent application and Korean priority patent applications are hereby incorporated herein by reference in their respective entireties, for all purposes.

TECHNICAL FIELD

The present invention relates to a novel polypeptide (repebody) capable of binding to interleukin-6 and to the use thereof. More particularly, the present invention relates to a repebody capable of binding to interleukin-6 to inhibit the activity of interleukin-6, a polynucleotide encoding the repebody, a vector comprising the polynucleotide, a host cell transformed with the vector, a method of producing the repebody by expressing the vector in the host cell, and a composition for preventing or treating cancer, which comprises the repebody.

BACKGROUND ART

Interleukin-6, a kind of cytokine, is a protein that is involved in a variety of biological activities, including immunity. In general people, interleukin-6 is present in blood at a concentration as low as 1 pg/ml and acts as a regulator important for vital phenomena. It is known that, if interleukin-6 is present in excessive amounts in vivo, it causes autoimmune diseases and tumors. It was reported that a typical disease caused by interleukin-6 is rheumatoid arthritis and that the concentration of interleukin-6 in the blood of patients having this disease is significantly higher than that in healthy people. It was reported that antibodies that bind specifically to interleukin-6 present in excessive amounts can inhibit the activity of interleukin-6, thereby exhibiting therapeutic effects on various diseases. Thus, a number of multinational pharmaceutical companies have made many efforts to develop monoclonal antibodies that can inhibit the binding between interleukin-6 and interleukin-6 receptor to inhibit signaling therebetween. Among them, the multinational pharmaceutical company Roche and the Japanese pharmaceutical company Chugai succeeded in the development of the therapeutic antibody Tocilizumab (trade name: ACTEMRA therapeutic antibody) that can bind to interleukin-6 receptor to inhibit the signaling of interleukin-6. This therapeutic antibody was approved by the FDA and is currently marketed as an agent for treating rheumatoid arthritis. In addition, a variety of therapeutic antibody candidates have entered clinical trials to evaluate the therapeutic effects thereof.

However, antibodies have problems, including low tissue penetration ability due to their high molecular weights, and high product costs due to complex production processes. For this reason, studies on new protein backbones capable of substituting for antibodies have recently been actively conducted. As a result, a protein, named "repebody", was developed. The repebody is a polypeptide prepared by fusing the N-terminus of internalin B having a leucine-rich repeat (LRR) structure with VLR based on the structural similarity therebetween so as to have a consensus design. The repebody is highly expressed in *E. coli* in the form of water-soluble monomer, and thus can reduce production costs. Also, it has high physical and chemical stabilities, and thus is easily modified. In addition, it is a novel protein backbone that has not been studied and developed, and thus is advantageously distinct from existing patents.

Under this background, the present inventors have made extensive efforts to develop repebody into a general-use binding protein backbone having a binding affinity for various proteins, and as a result, have selected a novel protein having a binding affinity for interleukin-6 based on a random mutation library constructed based on the analysis of the structural characteristic (modularity) and overall structure of repebody. In addition, the present inventors have prepared and selected a novel polypeptide (repebody) having a higher binding affinity for interleukin-6 through a repeat module-based affinity amplification method or a beneficial mutation predicted based on a protein complex structure, and have found that the repebody can prevent or alleviate cancer, thereby completing the present invention.

DISCLOSURE OF INVENTION

Technical Problem

It is an object of the present invention to provide a novel repebody capable of binding specifically to interleukin-6 to inhibit the biological activity of interleukin-6.

Another object of the present invention is to provide a polynucleotide encoding the repebody.

Still another object of the present invention is to provide a vector comprising the repebody, a recombinant microorganism having introduced therein the repebody and the vector comprising the repebody, and a method of producing the repebody using the recombinant microorganism.

Still another object of the present invention is to provide a composition for preventing or treating cancer, which contains the repebody.

Still another object of the present invention is to provide a method for preventing or treating cancer, the method comprising administering the composition for preventing or treating cancer, which contains the repebody.

Yet another object of the present invention is to provide the use of the repebody for preventing or treating cancer.

Technical Solution

To achieve the above objects, the present invention provides a novel repebody capable of binding to interleukin-6 to inhibit the activity of interleukin-6, a polynucleotide encoding the repebody, a vector comprising the polynucleotide, a host cell transformed with the vector, a method of producing the repebody by expressing the vector in the host cell.

The present invention provides a composition for preventing or treating cancer, which comprises the repebody and a method of preventing, or treating cancer comprising administering a composition for preventing or treating cancer comprising the repebody.

The present invention provides a use of the repebody in preventing or treating cancer.

The repebody of the present invention can bind to IL-6 with an affinity higher than that of naturally occurring IL-6 receptor (IL-6Ra) to significantly reduce the activity of STAT3 and the concentration of interleukin-6, and thus can be widely used for the development of agents for preventing or treating IL-6-related diseases.

BRIEF DESCRIPTION OF THE DRAWINGS

In FIG. 2, E is the number of eluate, and 27 KDa in the middle portion indicates a location in the standard marker used.

BEST MODE FOR CARRYING OUT THE INVENTION

Figure 1:
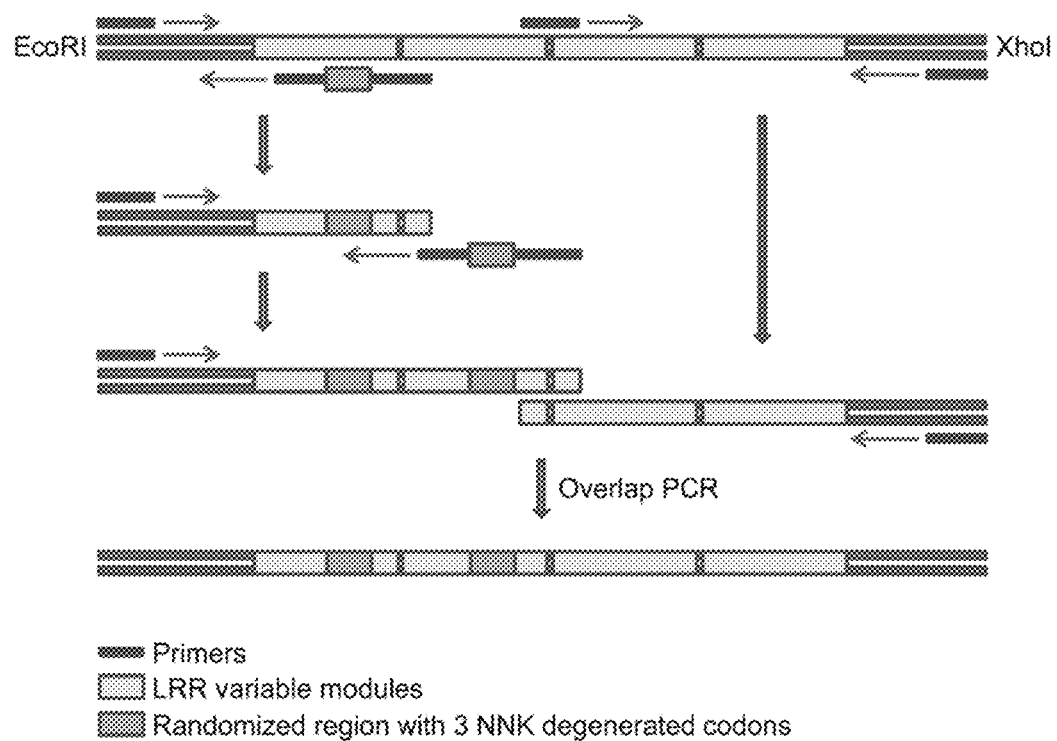
FIG. 1 is an overall schematic view showing an overlap polymerase chain reaction performed based on modules. Each yellow portion is a variable repeat module, and a total of four variable repeat modules are located on a polypeptide. The linear bars indicated by a red color are primers used in the experiment, and a green portion in the primers indicates the sequence of a concave area including a NNK consensus codon.

The present invention is directed to a novel repebody capable of binding specifically to interleukin-6 to inhibit the biological activity of interleukin-6, a polynucleotide encoding the repebody, a vector comprising the repebody, a recombinant microorganism having introduced therein the vector, and a method of producing the repebody using the recombinant microorganism.

In addition, the present invention is directed to a composition for preventing or treating cancer, which contains the repebody, and a method for preventing or treating cancer, the method comprising administering the composition for preventing or treating cancer, which contains the repebody.

In addition, the present invention is directed to the use of the repebody for preventing or treating cancer.

the present invention provides a repebody capable of binding to interleukin-6 to inhibit the activity of interleukin-6, which comprises an amino acid sequence of any one of SEQ ID NOS: 9 and 11 to 28 and is able to effectively bind to interleukin-6 (IL-6) to inhibit the activity of IL-6.

In order to develop a novel polypeptide (repebody) capable of effectively binding to IL-6 to inhibit the activity of IL-6, the present inventors constructed a library randomly comprising the repeat module of the polypeptide that comprises a fusion of the N-terminal of leucine-rich repeat (LRR) family protein, which is of microbial origin and has an alpha-helix capping motif, and the leucine-rich repeat (LRR) protein domain of variable lymphocyte receptor (VLR).

Here, in the present invention, the N-terminal of Leucine rich repeat (LRR) family protein, which is of microbial origin and has an alpha-helix capping motif, is preferably an N-terminal of an internalin protein. In the present invention, the term "internalin protein" is a kind of the LRR family protein expressed in a *Listeria* strain, and it is known that the internalin protein has an N-terminal structure different from that of the LRR family proteins in which a hydrophobic core are uniformly distributed through the entire molecule to thereby be stably expressed in microorganisms. It is considered that since the N-terminal of the internalin protein which is the most important in folding a repeat module is derived from a microorganism and has a stable shape including an alpha-helix, such that the internalin protein is stably expressed in microorganisms. The internalin protein used in fusion of the present invention may limitlessly include any internalin protein which is expected to have an N-terminal structure similar thereto and play an important role in protein folding, and as an example thereof, internalin protein A, B, C, H, J, or the like, preferably, internalin protein B, may be used. However, since the internalin proteins A to J are significantly similar to the internalin protein B in view of a structure, and the root mean square deviation (RMSD) values thereof with the N-terminal (36 to 11) of the internalin protein B through a structure alignment are 0.6 [internalin protein A (36 to 115)], 0.793 [internalin protein C (36 to 115)], 0.619 [internalin protein H (36 to 115)], and 0.862 [(internalin protein J (57 to 131)), respectively, which are significantly similar to that of internalin protein B, the internalin proteins A to J may be used instead of the internalin protein B.

In the present invention, the term "N-terminal of an (or the) internalin protein" of the present invention means an N-terminal of the internalin protein required for soluble expression and folding of the protein, and means the alpha-helix capping motif and a repeat module of the internalin protein. The N-terminal of the internalin protein may include any N-terminal of the internalin protein required for soluble expression and folding of the protein, and as an example thereof, an alpha-helix capping motif "ETITVSTPIKQIF-PDDAFAETIKANLKKKSVTDAVTQNE (SEQ ID NO: 9)" and the repeat module may be included, but is not limited thereto. The repeat module pattern may be "LxxLxxLx-LxxN". In the repeat module, L means alanine, glycine, phenylalanine, tyrosine, leucine, isoleucine, valine, or tryptophan; N means asparagine, glutamine, serine, cysteine or threonine; and x means any hydrophilic amino acid. In addition, the N-terminal of the internalin protein of the present invention may be the N-terminal of the internalin B protein which is SEQ ID NO: 30; however, may be limitlessly used as long as the N-terminal has high structural similarity depending on a kind of the LRR family protein, and the most stable amino acid may be selected by calculation of a binding energy, and the like, and the amino acid of the module corresponding thereto may be mutated. The N-terminal of the internalin protein selected by the method according to the present invention may consist of any one amino acid sequence selected from SEQ ID NOs: 31 to 49. SEQ ID NOs: 31 to 49 correspond to position Nos: 1 to 83 of the amino acid of SEQ ID NOs: 9, 11 to 28. A method for selecting the N-terminus of internalin protein will be described in further detail below.

The polypeptide included in the library according to the present invention may be encoded by a polynucleotide sequence of SEQ ID NO: 1 or a polynucleotide sequence having a homology of 75%, preferably 85%, more preferably 90%, further preferably 95% or more, with the polynucleotide sequence of SEQ ID NO: 1.

In addition, the library may be formed of phagemid including the polynucleotide. In the present invention, the term "phagemid" means a circular polynucleotide molecule derived from a phage which is a virus having *E. coli* as a host and includes sequences of proteins and surface-proteins required for propagation and proliferation. A recombinant phagemid may be produced using gene recombinant technology well known in the art, and site-specific DNA cleavage and connection may be performed by an enzyme, generally known in the art, and the like. The phagemid may include a signal sequence or leader sequence for secretion in addition to expression regulating factors such as a promoter, an operator, an initiation codon, a termination codon, an enhancer and may be mainly used in a method for labeling the protein on a surface of the phage by fusing a desired protein with a surface protein of the phage. The promoter of the phagemid is mostly inducible and may include a selective marker for selecting a host cell. For an object of the present invention, the phagemid may be a polynucleotide of SEQ ID NO: 2, including MalEss, DsbAss or PelBss which is a signal sequence or a leader sequence for expressing and secreting the polynucleotide which encodes the polypeptide constructing the library, and including a histidine-tag for confirming expression of a recombinant protein on a surface of the phage, and a polynucleotide which encodes gp3 domain which is a kind of a surface protein of M13 phage for expression on the surface of the phage, but the present invention is not particularly limited thereto.

The present inventors firstly selected a novel polypeptide (SEQ ID NOs: 3-6) which is a repebody having an excellent binding affinity for IL-6, using a phage display method using the library including the phagemid. However, these selected polypeptides showed low binding affinities for IL-6 compared to naturally occurring IL-6 receptor (IL-6Ra), and for this reason, the selected polypeptides were mutated in order to construct mutants having increased binding affinities for IL-6. Specifically, four amino acid residues in the polypeptide of SEQ ID NO: 5, which has the highest binding affinity among the selected polypeptides, were mutated to construct a second library (FIG. 8). Using a phage display method based on the second library, repebody-type novel polypeptides (SEQ ID NOS: 8 to 10) having high binding affinities for IL-6 were secondarily selected (FIG. 9). Among the secondarily selected polypeptides, the polypeptide of SEQ ID NO: 9 was mutated in the same manner to construct a third library (FIG. 11). Using a phage display method based on the third library, repebody-type novel polypeptides (SEQ ID NOS: 11 to 21) having high binding affinities for IL-6 were tertiarily selected (Table 1).

In addition, a repebody having an excellent binding affinity was secured by a rational design scheme based on a complex structure of the selected polypeptide and IL-6 protein. In detail, among the selected polypeptide amino acid sequence of SEQ ID NO: 9 having the most excellent binding affinity, an amino acid at a position which is expected to improve the binding affinity for IL-6 was mutated to obtain a novel polypeptide (SEQ ID NOs: 22-28) specifically bound to IL-6. That is, a complex of the polypeptide of SEQ ID NO: 9 and IL-6 was expressed in *E. coli* and the amino acid of the repebody adjacent to IL-6 was partially mutated, thereby selecting a polypeptide having an increased affinity to IL-6 based on the complex structure. In an exemplary embodiment of the present invention, polypeptides of which (an) amino acid(s) at one or two or more position(s) selected from a group consisting of Nos: 82, 84, 126, 182, 222 and 244 in polypeptide amino acid sequence represented by Repebody-D3E8 (SEQ ID NO: 9) is mutated were produced and among them, polypeptides of SEQ ID NOs: 22 to 28 were selected (see Table 2). The novel polypeptide (SEQ ID NOs: 22 to 28) produced by mutation of the amino acid of SEQ ID NO: 9 at a specific position can significantly suppress the concentration of IL-6 and the activity of STAT3 (signal transduction and activator of transciption3), and thus is useful for prevention and treatment of cancers.

As used herein, the term "interleukin-6 (IL-6)" refers to a glycoprotein having a molecular weight of 210,000 and isolated with B cell stimulatory factor-2 (BSF-2) that induces the final differentiation of B cells into antibody-producing cells. It is a kind of cytokine that is produced in various cells, including T lymphocytes, B lymphocytes, macrophages, fibroblasts and the like, and is involved in immune responses, the proliferation and differentiation of cells of the hematopoietic system and the nervous system, acute reactions, the growth and differentiation of various cells, etc.

In the present invention, the term "repebody" is a polypeptide optimized by consensus design through fusion of the N-terminal of the internalin B having the LRR protein structure and the VLR based on the structural similarity. The repebody protein may be structurally divided into a concave region and a convex region (FIG. 4). Here, it is known that the concave region has high variety of the sequence and is important in protein interaction. On the contrary, the convex region serves to stably maintain the entire structure of protein based on the highly conserved sequence. The repebody protein may include all fusion LRR family protein obtained by using all proteins included in the LRR family having the repeat module to improve the solubility expression and biophysical properties of protein of all protein by the above-described method.

In the present invention, the term "Leucine rich repeat (LRR) family protein" means a protein formed by combination of modules in which leucine is repeated at a certain position, (i) it has one or more LRR repeat modules, (ii) the LRR repeat module consists of 20 to 30 amino acids, (iii) the LRR repeat module has "LxxLxxLxLxxN" as a conservation pattern, wherein L means hydrophobic aminoacids such as alanine, glycine, phenylalanine, tyrosine, leucine, isoleucine, valine, and tryptophan; N means asparagine, glutamine, serine, cysteine or threonine and x means any amino acid, and (iv) the LRR family protein means a protein having a three dimensional structure like horseshoe. The LRR family protein of the present invention may include all mutants having the sequence which is already known or found by newly induced mRNA or cDNA, as well as the sequence which is not known in the natural world through consensus design, and the like, and having a frame of the repeat module, and as a non-limited example thereof, a variable lymphocyte receptor (VLR), a toll-like receptor (TLR), a TV3 protein, an U2A or ribonuclease inhibitor (RI) may be included. In a preferred exemplary embodiment of the present invention, the LRR family protein may include a number of repeat modules as long as fused water soluble polypeptide is capable of being stably expressed, but the number thereof is not limited thereto, wherein the number thereof is preferably 1 to 9. In addition, the number of the LRR repeat modules may be all numbers including the number known in the natural world as well as the numbers in which the frame of the fused polypeptide is capable of being maintained while artificially adding or removing the module.

In the present invention, the modified repeat module of the VLR protein may include the following repeat module pattern:

LxxLxxLxLxxN.

In the above pattern, L is alanine, glycine, phenylalanine, tyrosine, leucine, isoleucine, valine, or tryptophan; N is asparagine, glutamine, serine, cysteine or threonine; and x is any amino acid.

In the present invention, the term "mutation" or "modification" may include all substitution, deletion, or insertion of amino acid residues; preferably, substitution of the existing amino acid residue with the other amino acid residue.

In an exemplary embodiment of the present invention, the polypeptide in which the modified repeat module of the VLR protein and the C-terminal of the VLR protein are fused is characterized by consisting of polypeptide amino acid sequences represented by any one of SEQ ID NOs: 50 to 68. SEQ ID NOs: 50 to 68 correspond to positions NOs: 84 to 273 of the amino acid of SEQ ID NOs: 9, 11 to 28.

In another aspect, the present invention is directed to a polynucleotide encoding the repebody. The polynucleotide may be a polynucleotide having a homology of 75%, preferably 85%, more preferably 90%, further preferably 95% or more to a polynucleotide sequence encoding amino acid sequences represented by SEQ ID NOs: 9, 11 to 28, and having a polypeptide activity specifically bound to IL-6, but the present invention is not limited thereto. In view of an object of the present invention, it is obvious that the polypeptide (repebody) specifically bound to IL-6 may include polypeptide wherein one or more amino acid residues in the repebody represented by SEQ ID NOs: 9, 11 to 28 is substituted, deleted, or added, which also falls within the scope of the present invention.

In another aspect, the present invention is directed to a vector which contains the polynucleotide (repebody).

In the present invention, the term "vector" may be a DNA product containing base sequence of polynucleotide encoding a target protein operably connected to an appropriate regulation sequence so as to express the target protein in a suitable host cell. The regulation sequence may include a promoter capable of initiating transcription, an any operator sequence for regulating transcription, a sequence encoding an appropriate mRNA ribosome binding site, and a sequence regulating termination of transcription and decoding and may be variously produced depending on a purpose. The promoter of the vector may be constitutive or inducible. The vector may be transfected into a suitable host and then may be replicated or may perform functions regardless of the host genome, and may be integrated into a genome itself.

The vector used in the present invention is not particularly limited as long as it is replicated in host cells, and may be any vector known in the art. Examples of the generally used vector may include plasmid, phagemid, cosmid, virus, and bacteriophage in a natural state or a recombinant state. For example, as the phage vector or the cosmid vector, pWE15, M13, λMBL3, λMBL4, λIXII, λASHII, λAPII, λt10, λt11, Charon4A, and Charon21A may be used, and as the plasmid vector, pBR-based, pUC-based, PBLUESCRIPTII-based phagemid cloning vector, PGEM®-based cloning vector, pTZ-based, pCL-based and pET-based, may be used. The vector usable in the present invention is not particularly limited but may be any known expression vector. Preferably, pACYC177, pACYC184, pCL, pECCG117, pUC19, pBR322, pMW118, pCC1BAC vectors, and the like, may be used. Most preferably, pACYC177, pCL and pCC1BAC vectors may be used.

In still another aspect, the present invention is directed to a recombinant microorganism in which the polynucleotide (repebody) or the vector which contains the polynucleotide (repebody) is introduced.

In the present invention, the term "recombinant microorganism" means a transfected cell in which a vector having polynucleotide encoding one or more target proteins is introduced into a host cell, or polynucleotide encoding one or more target proteins is introduced into a microorganism, such that the polynucleotide is integrated into the chromosome to express the target protein, and may include all cells of eukaryotic cells, prokaryotic cells, and the like. Examples thereof may include bacteria cells such as *E. coli, streptomyces, salmonella typhimurium*, and the like; yeast cells; fungus cells such as pichiapastoris, and the like; insect cells such as *drosophila, spodoptera* Sf9 cell, and the like; animal cells such as CHO, COS, NSO, 293, bow melanoma cell, and the like, but the present invention is not particularly limited thereto.

In the present invention, the term "transfection" means that a vector containing polynucleotide encoding a target protein is introduced into a host cell, or a polynucleotide encoding a target protein is integratedly completed into chromosome of the host cell, such that protein encoded by the polynucleotide is capable of being expressed in the host cell. The transfected polynucleotide may be any one regardless of the position as long as the polynucleotide is capable of being expressed in the host cell, regardless of the matter that the polynucleotide is inserted and positioned into chromosome of the host cell or positioned on an outer portion of the chromosome. In addition, the polynucleotide includes DNA and RNA encoding the target protein. The polynucleotide may be inserted with any type as long as the polynucleotide is capable of being introduced into the host cell to be expressed. For example, the polynucleotide may be introduced into the host cell as an expression cassette which is a gene structure, including all factors required for self expression. The expression cassette may include a promoter, transcription termination signal, ribosome binding site and translation termination signal which may be operably connected to the polynucleotide. The expression cassette may be an expression vector performing self-replication. In addition, the polynucleotide may be introduced into the host cell as itself to be operably connected to the sequence required for expression in the host cell.

In still another aspect, the present invention is directed to a method for producing a repebody against IL-6, wherein the method comprises: (i) expressing the repebody by culturing a transformant; and (ii) recovering the expressed repebody.

In the method, the culturing of the transformant may be preferably performed by a batch culture method, a continuous culture method, a fed-batch culture, and the like, known in the art, but the present invention not particularly limited thereto, wherein under the culture condition, pH may be appropriately adjusted (pH 5 to 9, preferably pH 6 to 8, most preferably pH 6.8) by using a basic compound (for example: sodium hydroxide, potassium hydroxide or ammonia) or an acidic compound (for example, phosphoric acid or sulfuric acid), and an aerobic condition may be maintained by introducing oxygen, or an oxygen-containing gas mixture into the culture, and the culture may be performed at 20 to 45° C., preferably, 25 to 40° C. for about 10 to 160 hours. The repebody produced by the culture may be secreted in the medium or remained in the cell.

In addition, in the culture medium used, as carbon source, sugar and carbohydrate (for example, glucose, sucrose, lactose, fructose, maltose, molasse, starch and cellulose), oil and fat (for example, soybean oil, sunflower seed oil, peanut oil and coconut oil), fatty acid (for example, palmitic acid, stearic acid and linoleic acid), alcohol (for example, glycerol and ethanol) and organic acid (for example, acetic acid), and the like, may be used individually or by mixing; as nitrogen source, nitrogen-containing organic compound (for example, peptone, yeast extract, gravy, malt extract, corn steep liquor, soybean meal powder and urea), or inorganic compound (for example, ammonium sulfate, ammonium chloride, ammonium phosphate, ammonium carbonate and ammonium nitrate) and the like, may be used individually or by mixing; as phosphate source, potassium dihydrogen phosphate, dipotassium hydrogen phosphate, sodium-containing salt corresponding thereof, and the like, may be used individually or by mixing; or essential growth-promoting materials such as other metal salts (for example, magnesium sulfate or iron sulfate), amino acids and vitamins may be included.

In the recovering of the repebody produced in the culturing of the present invention, the desired repebody may be recovered from a culture fluid by appropriate culture methods such as a batch culture method, a continuous culture method, a fed-batch culture, and the like, known in the art.

In another aspect, the present invention is directed to a composition for preventing or treating cancer, which comprises the repebody.

As used herein, the term "cancer" or "tumor" refers to a mass caused by the abnormal growth of body tissue. Because interleukin-6 is a growth factor that induces tumor proliferation and angiogenesis, the term "cancer" or "tumor" as used herein is meant to include all non-small-cell lung cancer, ovarian cancer, multiple myeloma, Castleman's disease, liver cancer and the like, which secrete an excessive amount of interleukin-6.

As used herein, the term "treating" refers to not only inhibiting or alleviating cancer or one or more symptoms caused thereby, but also treating cancer or preventing the progression of cancer, by administering the composition. As used herein, the term "preventing" refers to all actions that inhibit cancer or delay the onset of cancer by administering the composition.

In the present invention, the prevention or treatment of cancer is achieved by the binding of the repebody of the present invention to interleukin-6. Specifically, cancer is prevented or treated by significantly inhibiting the serum interleukin-6 concentration and the activity of STAT3 (signal transduction and activator of transcription3).

Interleukin-6 is known as the most important growth factor that induces tumor proliferation and angiogenesis. Also, it is known as an important mediator for cytokine networks in human tumors such as non-small-cell lung cancer, ovarian cancer, multiple myeloma, Castleman's disease, liver cancer and the like. Specifically, it is known that (1) the serum interleukin-6 level and the expression level of interleukin-6 receptor are closely associated with cancer development, (2) no tumor development occurs in interleukin-6-deficient mice, (3) cancer development is decreased when an anti-interleukin-6 monoclonal antibody is administered to a patient, (4) the proliferation of multiple myeloma cells in vitro is inhibited when the cells are treated with an interleukin-6 or interleukin-6 receptor neutralizing monoclonal antibody, (5) the proliferation of plasma cells is inhibited when interleukin-6 messenger RNA is inhibited with interleukin-6 small interfering RNA (siRNA), and (6) cytokines, such as interleukin-1, interleukin-3, and granulocyte macrophage colony-stimulating factor, act together to exhibit a synergistic effect on tumor cell proliferation and induce the production of interleukin-6 in a tumor development environment.

However, it has not been known that repebody is effective as a tumor treating agent. Accordingly, in order to evaluate the biological activity of the repebody of the present invention, the present inventors used non-small-cell lung cancer cells as an experimental model, and treated the non-small-cell lung cancer cells with varying concentrations of the repebody of the present invention, and also analyzed (1) whether the activity of STAT3 is decreased, (2) whether the production of interleukin-6 is inhibited, and (3) whether a tumor in xenograft mice treated with non-small-cell lung cancer cells is inhibited. The results of all the three analysis items indicated that the repebody of the present invention has tumor inhibitory activity, suggesting that the repebody according to the present invention can kill tumor cells by inhibiting the production of interleukin-6 and the activity of STAT3. Specifically, in an example of the present invention, it was shown that repebodies having polypeptides of SEQ ID NOS: 22 to 28 had high binding affinities for IL-6 (see Table 2) and that when repebody-D3E8 (I82K) (SEQ ID NO: 22) and repebody-D3E8-KE (SEQ ID NO: 28) were added to non-small-cell lung cancer cell media, the STAT3 activity (P-STAT3) and interleukin-6 concentration of the cells significantly decreased in a concentration-dependent manner (see Example 3 and FIG. 2). Such results demonstrate that the repebody of the present invention can effectively bind to interleukin-6 to inhibit the activity of STAT3, thereby preventing or treating cancer. In contrast, it could be seen that the inhibitory effects of D3E8 (SEQ ID NO: 9), D3 (SEQ ID NO: 10) and repebody-D3E8C4 (SEQ ID NO: 15) on the activity of STAT3 and the concentration of IL-6 were insufficient compared to those of the repebodies having polypeptides of SEQ ID NOS: 22 to 28. Thus, the repebody according to the present invention can be effectively used for the prevention or treatment of cancer. Further, in an example of the present invention, only an example for non-small-cell lung cancer was disclosed, but the repebody of the present invention can significantly inhibit the concentration of interleukin-6 and the activity of STAT3, and thus it is obvious that the repebody of the present invention can also be used for the prevention or treatment of interleukin-6-related diseases in addition to cancer.

A composition for preventing or treating sepsis, which comprises the repebody of the present invention, may further comprise a pharmaceutically acceptable carrier and may be formulated with a carrier.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets.

A composition for preventing or treating cancer, which comprises the repebody of the present invention and a pharmaceutically acceptable carrier, can be applied as any formulation comprising it as an active ingredient and may be prepared as an oral or parenteral formulation. Pharmaceutical formulations of the present invention include those suitable for oral, rectal, nasal, topical (including buccal and sublingual), vaginal or parenteral (including intramuscular, subcutaneous and intravenous) administration or a form suitable for administration by inhalation or insufflation.

Examples of oral formulations comprising the composition of the present invention as an active ingredient include tablets, troches, lozenges, aqueous or emulsified suspensions, powders, granules, emulsions, hard or soft capsules, syrups, or elixirs. Formulations such as tablets or capsules may include a binder such as lactose, saccharose, sorbitol, mannitol, starch, amylopectin, cellulose or gelatin, an expedient such as dicalcium phosphate, a disintegrant such as corn starch or sweet potato starch, and a lubricant such as magnesium stearate, calcium stearate, sodium stearyl fumarate or polyethylene glycol wax. Capsule formulations may comprise, in addition to the above-mentioned substances, a liquid carrier such as fatty oil.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas, e.g. containing conventional suppository bases such as cocoa buffer or other glycerides. For spray formulations, such as aerosols, a propellant for spraying a water-dispersed concentrate or wet powder may be used in combination with an additive.

In another aspect, the present invention is directed to a method for preventing or treating cancer, the method comprising administering the composition for preventing or treating cancer, which comprises the polypeptide.

As used herein, the term "administration" means introducing a desired material into a patient by any suitable method. The composition of the present invention may be administered through various routes such as an oral or parenteral route, as long as it can reach a desired tissue. For example, the composition of the present invention may be administered in a conventional manner via an oral, rectal, topical, intravenous, intraperitoneal, intramuscular, intravenous, transdermal, intranasal, inhalation, intraocular or intradermal route.

The treatment method of the present invention includes administering the composition for preventing or treating cancer of the present invention in a therapeutically effective amount. In the present invention, the "therapeutically effective amount" refers to the amount of the composition that is physiologically acceptable and does not cause gastric disorder, allergic reactions such as gastrointestinal disorder or vertigo, or similar reactions, when the composition is administered to humans. It is apparent to those skilled in the art that the suitable total daily dose of the composition can be determined by an attending physician or veterinarian within the scope of sound medical judgment. The specific therapeutically effective amount for any particular patient will depend upon various factors including the type and extent of response to be achieved, specific compositions according to whether other agents are used therewith or not, the patient's age, body weight, health condition, sex and diet, the time and route of administration, the secretion rate of the composition, the duration of treatment, other drugs used in combination or coincident with the composition, and other similar factors well-known in the medical field. Thus, the therapeutically effective amount of the composition for preventing or treating cancer, which is suitable for the purpose of the present invention, is preferably determined by taking into consideration the above-described factors.

In addition, the inventive method for treating cancer may be applied to any animal in which STAT3 can be continuously activated due to the excessive secretion of interleukin-6 to cause diseases including tumor development and angiogenesis. Examples of animals to which the inventive method may be applied include humans and primate mammals, as well as livestock animals such as cows, pigs, sheep, horses, dogs and cats.

EXAMPLES

Hereinafter, the present invention will be described in further detail with reference to examples. It will be obvious to a person having ordinary skill in the art that these examples are illustrative purposes only and are not to be construed to limit the scope of the present invention. In addition, it will be apparent to those skilled in that art that various modifications and variations can be made without departing from the technical scope of the present invention based on this illustration.

Example 1: Design of Phagemid for Selection of Random Repebody Library

A protein frame named repebody was used as a component of the present invention. The frame is a water soluble polypeptide in which an LRR portion containing an N-terminal of an internalin B protein and a C-terminal of VLR protein is fused, and has an amino acid sequence the same as SEQ ID NO: 7.

Example 1-1: Expression of Repebody Using Signal Sequence in Periplasm

In order to confirm whether or not the repebody is applicable to a phage display, it is required to confirm periplasmic expression of E. coli to be used as a host, and whether or not protein is well expressed onto a surface particle of a phage. To this end, two recombinant vectors were produced by inserting MalE and DsbA signal sequences which are signal polypeptides differentiated from each other right into the back side of an initiation codon, using PMAL-C2X (NEB, USA) plasmid vector. Then, DNA in which the repebody and a histidine-tag are fused was inserted between the signal sequence and termination codon to complete a final vector. Two completed vector was introduced into E. coli XL1-BLUE cloning cell strain to produce a transformant, the transformant was cultured until absorbance ($OD_{600}$) reached 0.5 and then 0.1 mM IPTG (Isopropyl β-D-1-thiogalactopyranoside) was treated to induce expression of the protein, followed by culturing at 30° C. for 16 hours again. After the culturing was completed, the strain was obtained by centrifugation and treated by ultrasonic wave to obtain a water soluble protein fraction.

Figure 2:
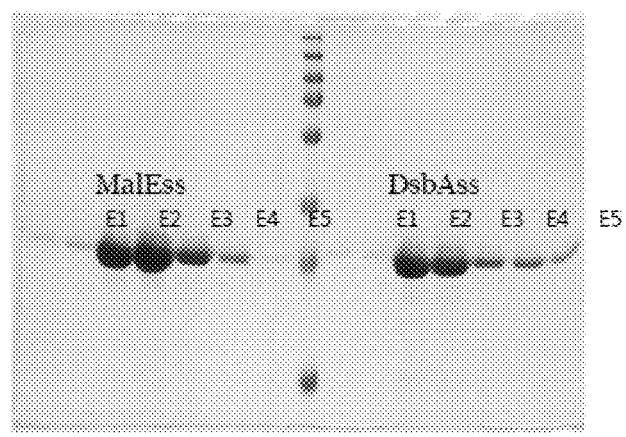
FIG. 2 shows the results of SDS-PAGE performed to confirm that repebody is expressed in periplasm through two different signaling sequences.

The obtained water soluble protein fraction was applied to a Ni-NTA (Nickel-nitrilotriacetic acid) resin to be purified, and an expression amount of the produced repebody in periplasm was confirmed by SDS-PAGE analysis (FIG. 2). FIG. 2 shows an examination result showing repebody expressed in periplasm through two different signal sequences, confirmed by SDS-PAGE, wherein E means the number of eluate, and 27KDa in the middle means a position of the used standard marker. As shown in FIG. 2, it was confirmed that the MalE signal sequence had a periplasmic expression amount slightly higher than that of the DsbA signal sequence.

Example 1-2: Construct of Phagemid for Repebody Expression on Surface of Phage A phagemid was designed based on the MalE signal sequence finally determined in Example 1-1 above. With pTV118N (Takara, Japan) as a basic frame, the MalE signal sequence was inserted right into the back side of the initiation codon and DNA in which the repebody and a histidine-tag are fused was added to thereby construct a phagemid. In addition, gp3 which is capable of labeling a relatively large protein among several phage surface proteins was used, C-terminal was positioned at the back of an amber codon, and two continuous terminal codons were finally inserted thereto, thereby completing the phagemid named pBEL118N. The phagemid was introduced into XL1-BLUE cloning cell strain to produce a transformant, and the produced transformant was cultured by the same method as Example 1-1 above except for treatment with 0.5 mM IPTG, followed by centrifugation to obtain a culture fluid.

The culture fluid was applied to Polyethylene glycol precipitation method to purify the phage.

Figure 3:
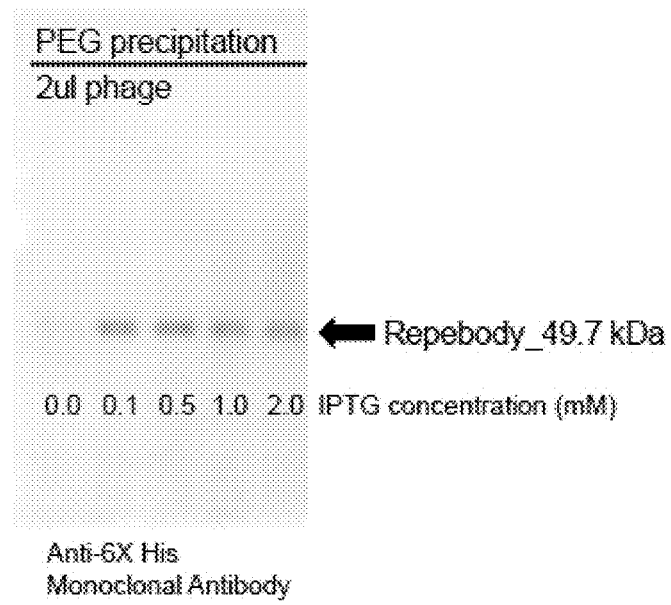
FIG. 3 shows the results of Western blot analysis performed using the phagemid pBEL118N of the present invention in order to confirm that repebody is expressed on the surface of phages. Herein, the unit mM indicates the concentration of IPTG used in promoter induction.

The phage was analyzed by Western Blot, and as a result thereof, it was confirmed that the repebody was expressed on a surface of the phage (FIG. 3). FIG. 3 is a view showing an analysis result of Western Blot for confirming that repebody is expressed on a surface of phage, using phagemid pBEL118N of the present invention, wherein the mM unit means a concentration of IPTG used in induction of the promoter.

Example 2: Construct of Repebody Library Based on Protein Structure

Figure 4:
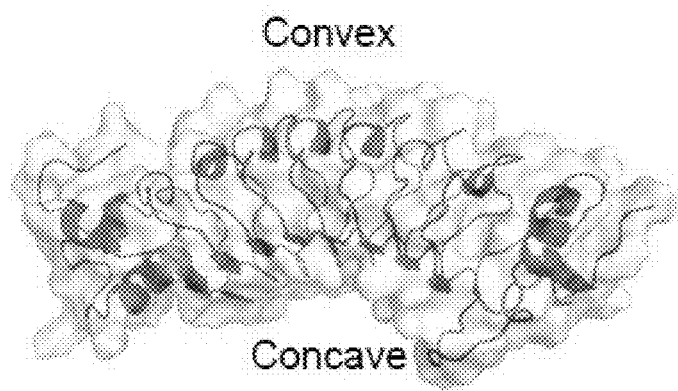
FIG. 4 is a schematic view showing the overall protein structure of repebody, which is divided into a concave area that recognizes a biopolymer, and a convex area important for the maintenance of the structure.

The repebody consists of continuously connected repeat units having conserved leucine sequence, similar to LRR proteins present in the natural world and has a modularity maintaining the entire protein structure and structural characteristic of a concave region and a convex region differentiated by curvature of the entire structure (FIG. 4). FIG. 4 is a schematic diagram showing an entire protein structure of repebody, divided into a concave region recognizing biomolecule and a convex region which is important in maintaining the structure. A hypervariable region like a complementarity determining region (CDR) was positioned in the concave region to mediate a protein-protein interaction. In addition, the convex region is important to maintain the entire structure of LRR based on the well conserved sequence. The protein structure of the repebody was analyzed and a random library was designed by the following scheme.

Figure 5:
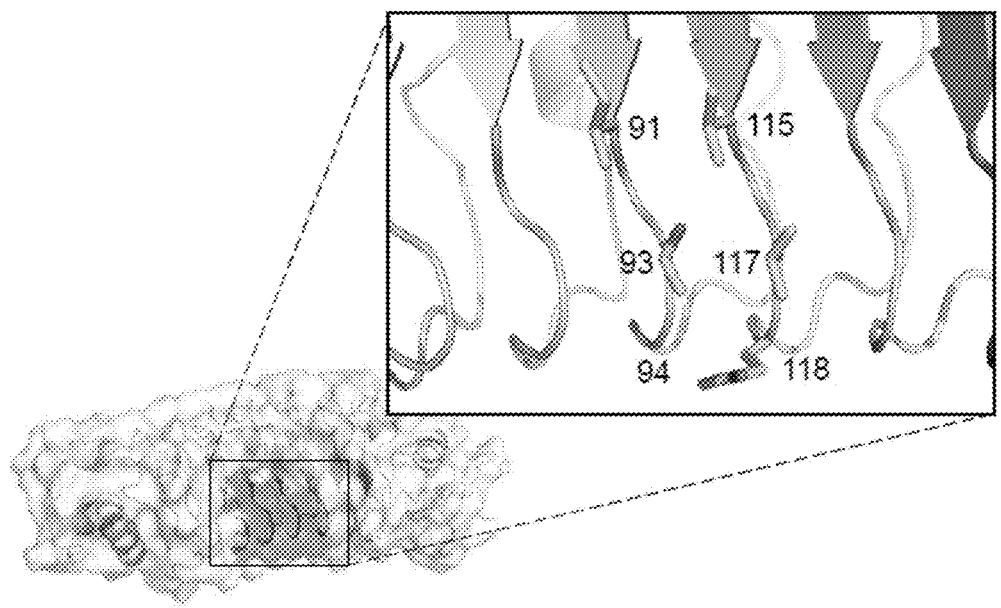
FIG. 5 is a schematic view showing an overall structure including indicated amino acid residues that are used to construct a random library.

In detail, six amino acid residues Nos. 91, 93, 94, 115, 117 and 118 positioned at the concave region of two continuous mutation modules (LRRV module 1 and 2) positioned at an amine group terminus were selected in order to deviate from steric hinderance by C-term loop of a non-designed carboxylic acid terminus (FIG. 5). FIG. 5 is a schematic diagram showing an entire structure including amino acid residues for constructing a random library.

Then, the selected amino acid was substituted with NNK degenerate codon and configured so that base sequences of the other convex region include silent mutation, thereby synthesizing a mutagenic primer for constructing a library.

Next, overlap PCR was performed on two modules using the primers to obtain a library DNA (FIG. 1) and the library DNA was inserted into the phagemid pBEL118N to secure a final library phagemid. FIG. 1 is a schematic diagram showing the entire overlap PCR performed based on a module. Each yellow part indicates a variable repeat module and a total of four variable repeat modules are positioned on a polypeptide. A red linear rod indicates a primer used in experiments and a green part of the primer indicates sequence of a concave region containing NNK degenerate codon.

The secured library was introduced into E. coli XL1-Blue by electroporation to obtain a transformant, such that a library having a synthetic diversity with a level of $1.8 \times 10^8$ was constructed.

Example 3: Selection of Protein Specifically Bound to IL-6 Using Phage Display

Example 3-1: Selection of Polypeptide Bound to IL-6 Through Purification and Panning of Repebody Library Phage The library constructed in Example 2 was cultured by the method of Example 1-1 above and the phage in which the repebody was expressed on a surface thereof was selected by the method of Example 1-2 and purified. In order to select a candidate capable of binding IL-6, 100 ug/ml of IL-6 was coated on an immuno tube at 4° C. for 12 hours or more. The coated tube was washed three times with PBS (Phosphate buffered saline), followed by blocking with a PBS solution (TPBS) containing 1% bovine serum albumin (BSA) and 0.1% TWEEN 20 nonionic surfactant at 4° C. for 2 hours. After the blocking, $10^{12}$ cfu (Colony forming unit)/ml of the purified phage was added to the coated tube and was reacted at room temperature for 2 hours. After the reaction has been completed, the reactant was washed with a PBS solution (TPBS) containing 0.1% TWEEN 20 nonionic surfactant total five times for 2 minutes and then washed again with PBC twice. Finally, 1 ml 0.2M Gly-HCl (pH2.2) was added to the immune tube, and the reactant was treated with 1 ml 0.2M Gly-HCl (pH2.2) at room temperature for 12 minutes to elute the phage having a candidate capable of binding to IL-6, expressed on the surface thereof in the tube. The reactant after the elution was neutralized with 60 ul of 1.0M Tris-HCl (pH9.1) and 10 ml XL1-BLUE cloning cell strain ($OD_{600}$=0.5) which is a host cell was inserted thereinto, followed by plating on a 2×YT plate. A bio-panning process through a series of process as described above was performed total of three times. As a result, a phenomenon that the phage specifically bound to IL-6 through each panning process is enriched was observed. The result means that the library phage bound to IL-6 is specifically increased.

Example 3-2: Confirmation of Whether the Selected Repebody Binds Specifically to IL-6, and Sequencing of the Selected Repebody The phages selected by the method of Example 3-1 were subjected to Enzyme-linked immunosorbent assay (ELISA) using a 96-well plate coated with IL-6 and BSA, thereby selecting 84 repebody candidates in which the absorbance (OD450) of IL-6 was at least 10 times higher than that of BSA. The amino acid sequence of each of the candidates was analyzed, and then WebLogo was performed to determine the consensus sequence. As a result, it was shown that residues having a high mutation frequency were present in the amino acid sequences of proteins that did bind specifically to IL-6 expressed in the selected phages.

Specifically, it was shown that the amino acid isoleucine at position 91 was substituted with tryptophan, valine or threonine, the amino acid threonine at position 93 was substituted with arginine or glutamic acid, the amino acid glycine at position 94 was substituted with alanine, serine or proline, the amino acid valine at position 115 was substituted with valine (silent mutation), serine, alanine or asparagine, the amino acid valine at position 117 was substituted with lysine or tryptophan, and the amino acid glutamic acid at position 118 was substituted with arginine, lysine or leucine.

Such results suggest that residues playing an important role in binding to IL-6 are present.

Example 4: Carrying Out of a Module-Based Affinity Amplification Method for Increasing the Binding Affinity of Repebody Example 4-1: Analysis of Characteristics of Repebody that Binds Specifically to Interleukin-6

Figure 6:
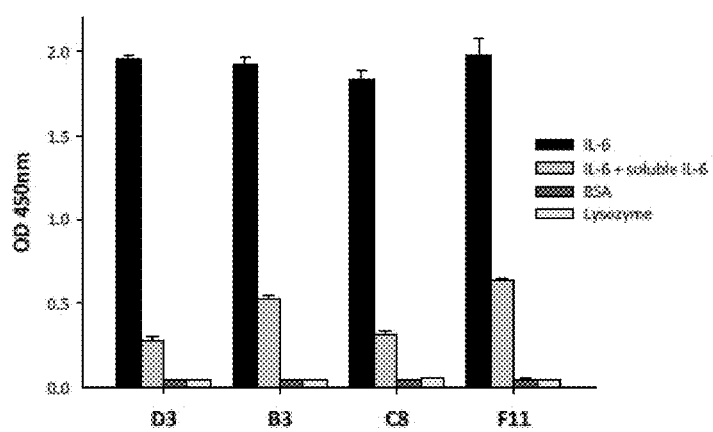
FIG. 6 shows the results of an enzyme immunoassay performed to confirm whether a peptide has specificity for the target protein.

Based on the results of the ELISA performed in Example 3-2, four candidates (repebody-B3 (SEQ ID NO: 3), repebody-C8 (SEQ ID NO: 4), repebody-D3 (SEQ ID NO: 5) and repebody-F11 (SEQ ID NO: 6)) that showed the highest absorbance for IL-6 among the selected repebody candidates were subjected to phage ELISA using plates coated with IL-6, lysozyme and BSA (FIG. 6). FIG. 6 shows the results of an enzyme immunoassay performed to examine whether the candidates has specificity for the target protein. As can be seen in FIG. 6, the four candidates have target specificity for IL-6.

Figure 7:
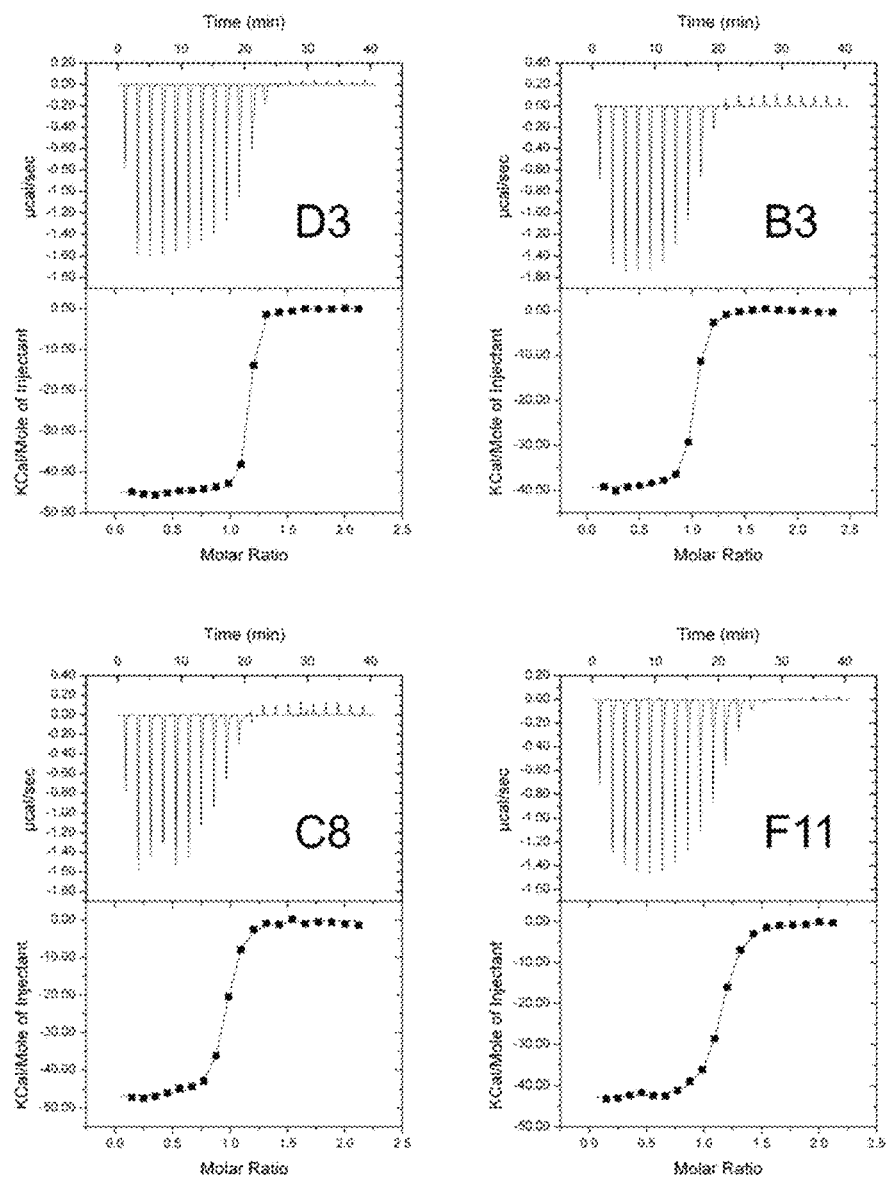
FIG. 7 is a figure and a table, which show the results of isothermal titration calorimetry performed to measure the binding affinity of the repebody of the present invention for interleukin-6.

Meanwhile, the dissociation constants of the four candidates for IL-6 were measured. Specifically, the dissociation constants of the four candidates for IL-6 at room temperature were measured by isothermal titration calorimetry (ITC) using the repebody, dissolved in PBS at 0.2 mM (6 mg/ml), and IL-6 dissolved in PBS at 0.02 mM (0.5 mg/ml) (FIG. 7). FIG. 7 is a figure and a table, which show the results of isothermal titration calorimetry performed to measure the binding affinity of the polypeptide of the present invention for interleukin-6.

As can be seen in FIG. 7, the dissociation constants (KD) of the four candidates for IL-6 were 17 nM for repebody-D3, 48 nM for repebody-B3, 89 nM for repebody-C8, and 117 nM for repebody-F11. Thus, it could be seen that, among the four candidates, repebody-D3 can most effectively bind to IL-6.

Example 4-2: Construction of Additional Libraries Using Modules and Confirmation of Increase in Binding Affinity The results of Example 4-1 indicated that the dissociation constant of repebody-D3 (that can most effectively bind to IL-6) for IL-6 is 17 nM, but the dissociation constant of naturally occurring IL-6 receptor (IL-6Ra) for IL-6 is 9 nM. Thus, in order for repebody to function as an inhibitor, the repebody should have a dissociation constant lower than 9 nM. Accordingly, it was thought that the repebody candidates of the present invention cannot sufficiently inhibit the activity of IL-6.

In order to solve this problem, the modularity of repebody was used to develop a mutant having an increased binding affinity for IL-6.

Figure 8:
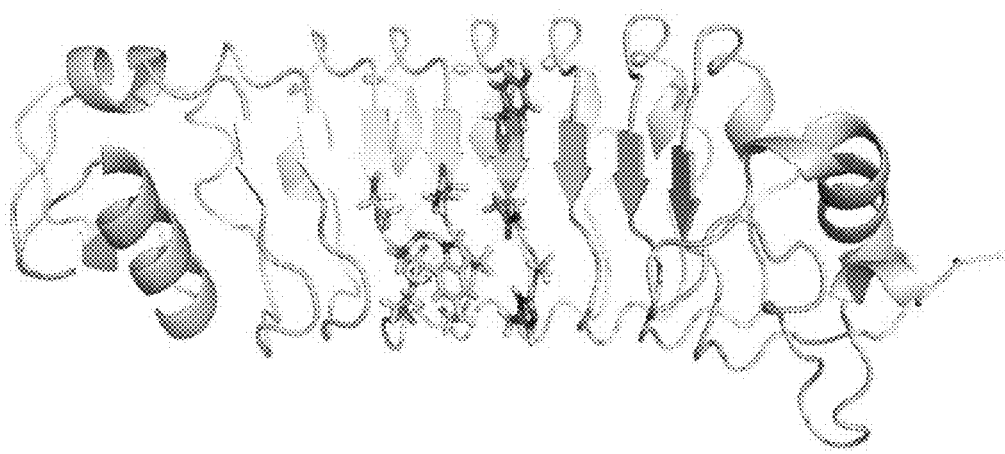
FIG. 8 is a schematic view showing a method for constructing a second library. Herein, the yellow residues indicate residues in an existing constructed library, and the green amino acids indicate the corresponding positions in a newly constructed library.
Figure 9:
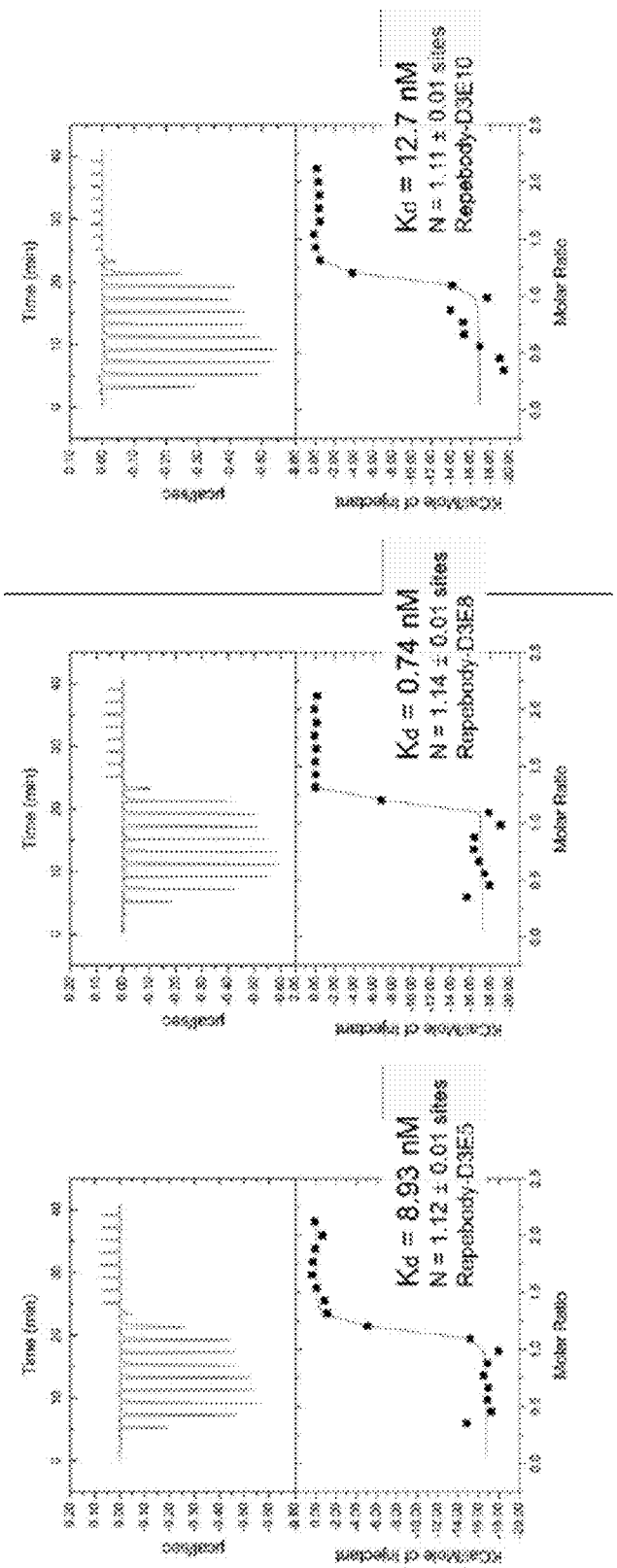
FIG. 9 is a graphic diagram showing the measured binding affinities of binding candidates screened based on a second library.

Specifically, the module (LRRV module 3) adjacent to the library area constructed in Example 2 was selected, and four residues in the concave area were mutated in the same manner as described in Example 2 (FIG. 8). FIG. 8 is a schematic view showing a method for constructing a second library. In FIG. 8, the yellow residues indicate residues in the existing constructed library, and the green amino acids indicate the corresponding positions in a newly constructed library. A total of panning processes were performed again to obtain three candidates (repebody-D3E5 (SEQ ID NO: 8), repebody-D3E8 (SEQ ID NO: 9) and repebody-D3E10 (SEQ ID NO: 10)), which have increased binding affinities. The dissociation constants of the candidates were measured by ITC, and as a result, it was shown that the binding affinities of the candidates were increased to a level of 2-13 nM (FIG. 9). FIG. 9 is a graphic diagram showing the measured binding affinities of the binding candidates selected based on the second library.

Figure 10:
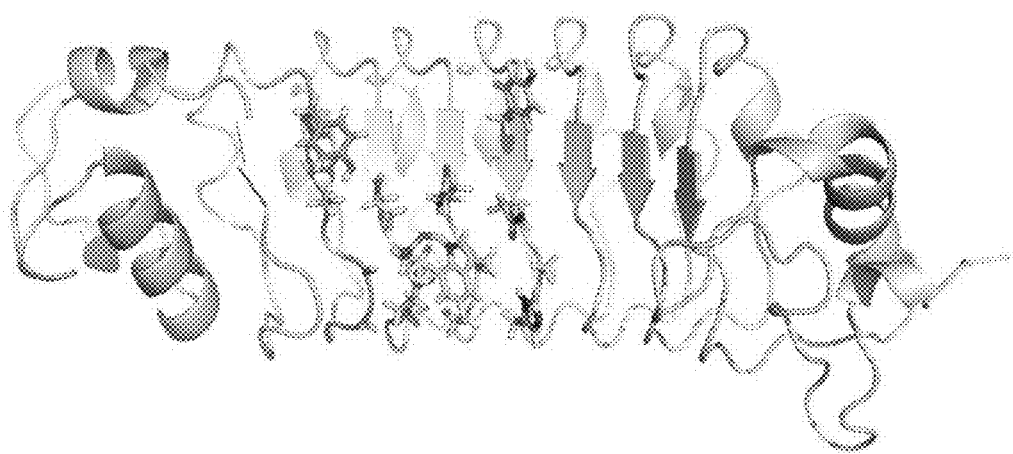
FIG. 10 is a schematic view showing a method for constructing a third library. Herein, the yellow residues indicate residues in an existing constructed library, and the green amino acids indicate the corresponding positions in a newly constructed library.

Meanwhile, in order to develop a mutant showing a higher binding affinity, a third library was constructed by performing the above-described method for the adjacent module (LRR2) in the internalin direction (FIG. 10). FIG. 10 is a schematic view showing a method for constructing the third library. In FIG. 10, the yellow residues indicate residues in the existing constructed library, and the green amino acids indicate the corresponding positions in a newly constructed library. Based on the third library, candidates having increased binding affinities were selected by phage display, and a candidate having a dissociation constant of about 400 pM was finally selected (Table 1).

TABLE 1

Sequences and binding affinities of repebody candidates

| Repebody | SEQ ID NOs | Position of mutation | | | | $K_{app}$ ($10^6$ M) | $K_p$ ($10^{-9}$ M) | Fold |
|---|---|---|---|---|---|---|---|---|
| | | 67 | 60 | 71 | 72 | | | |
| D3E8 | 9 | Y | A | G | G | 2.35 | 2.47 | 1.0 |
| D3E8B2 | 11 | Y | T | V | Q | 4.90 | 1.18 | 2.1 |
| D3E8B3 | 12 | Y | T | Q | S | 6.11 | 0.949 | 2.6 |
| D3E8B4 | 13 | Y | T | T | N | 3.24 | 1.04 | 1.4 |
| D3E8B8 | 14 | Y | T | R | N | 3.06 | 1.90 | 1.3 |
| D3E8C4 | 15 | K | T | V | S | 14.6 | 0.397 | 6.2 |
| D3E8C7 | 16 | Y | T | I | T | 4.47 | 1.30 | 1.9 |
| D3E8C9 | 17 | Y | A | S | S | 10.7 | 0.542 | 4.6 |
| D3E8C11 | 18 | Y | S | I | N | 1.88 | 3.09 | 0.8 |
| D3E8H2 | 19 | Y | L | R | S | 5.58 | 1.43 | 2.4 |
| D3E8H3 | 20 | M | I | R | S | 4.05 | 1.79 | 1.7 |
| D3E8H5 | 21 | Y | M | R | S | 5.12 | 1.13 | 2.2 |

Such results indicated that a repebody library can be reasonably designed using the inherent characteristic (modularity) of the repeat protein, unlike conventional antibodies, and that the binding affinity of repebody for the target protein can be effectively increased by constructing libraries based on sequentially adjacent modules.

Example 5: Carrying Out of Reasonable Design for Increasing the Binding Affinity of Repebody Based on Complex Structure Repebody-D3E8 (SEQ ID NO: 9) obtained in Example 4 was used as a polypeptide for a reasonable design. The polypeptide repebody-D3E8 (SEQ ID NO: 9) binds to IL-6 with an affinity corresponding to a dissociation constant of 2.7 nM.

Example 5-1: Construction of Repebody/IL-6 Complex Structure

Figure 11:
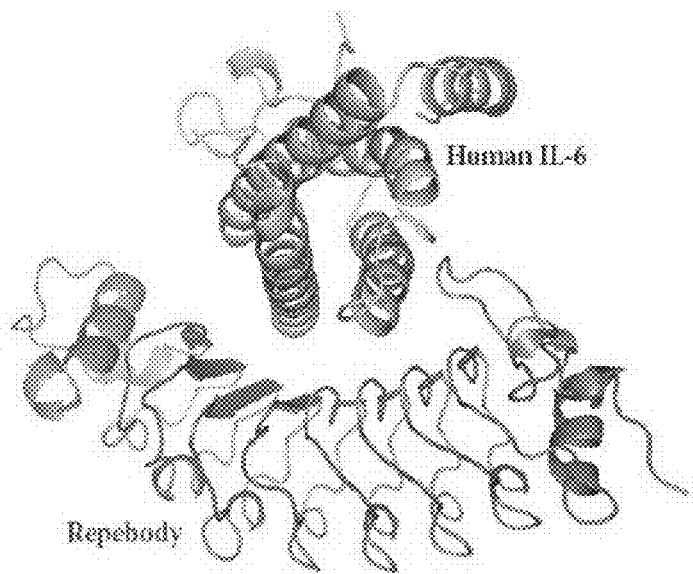
FIG. 11 is a schematic view showing the crystallized structure of a complex of repebody and interleukin-6.

For a reasonable design, repebody-D3E8 and IL-6 were expressed in *E. coli*. The polypeptide repebody-D3E8 was purified using a Ni-NTA column and gel permeation chromatography (GPC), and then the complex was reacted in crystallization buffer (0.1M magnesium formate, 15-18% PEG3350) at a total concentration of 60 mg/ml at 17° C., thereby obtaining a crystalline structure. The structure of the complex was observed by an X-ray diffraction method (see FIG. 11, resolution: 2.3 Å).

Example 5-2: Analysis of Interaction Between Proteins Based on Complex Structure Based on the complex structure obtained in Example 5-1, each residue in the repebody was analyzed. As a result, it could be seen that electrostatic interaction is a major factor related to binding affinity. It was judged that the optimization of electrostatic interaction can lead to an increase in the interaction between proteins. Based on this judgment, the present inventors analyzed the interaction type of repebody residue positioned adjacent to IL-6 in the complex structure.

Example 5-3: Reasonable Design for Increasing the Binding Affinity of Repebody, Based on the Results of Structural Analysis Based on the results of analysis performed in Example 5-2, the present inventors performed a process for optimizing the electrostatic interaction between repebody residues. It was found that, among the amino acids of repebody close to IL-6, isoleucine at position 82 and asparagine at position 84 were positioned close to positively charged glutamic acid. Thus, each of the amino acids at positions 82 and 84 was substituted with positively charged lysine. Changes in the affinities of the mutations for IL-6 were observed by isothermal titration calorimetry (ITC) (Table 2). Because threonine at position 126 was adjacent to a hydrophobic site comprised of tryptophan at position 152, it was substituted with valine in order to induce further enhanced hydrophobic binding. Also, arginine at position 222 and tyrosine at position 244 were positioned close to positively charged arginine and lysine, respectively, and thus these residues were substituted with negatively charged glutamic acid having a relatively long length. Based on a reasonable design method that optimizes electrostatic interaction based on the results of the above-described structural analysis, it was found that all repebodies excluding asparagine at position 84 had a dissociation constant of about 50-9300 pM. In other words, the repebodies had an increased binding affinity for IL-6. Among them, repebody-D3E8-KE (SEQ ID NO: 28) had a dissociation constant of 63 pM, suggesting that it can effectively bind to interleukin-6.

TABLE 2

| Repebody | SEQ ID NOs | Mutation | Interaction Type | $K_p$ (pM) |
|---|---|---|---|---|
| Rb-D3E8 | | | | 2470 |
| D3E8 (I82K) | 22 | I82K | Ionic | 117 |
| D3E8 (N84K) | 23 | N84K | Ionic | 9300 |
| D3E8 (T126V) | 24 | T126V | Hydrophobic | 240 |
| D3E8 (R222E) | 25 | R222E | Ionic | 214 |
| D3E8 (Y244E) | 26 | Y244E | Ionic | 236 |
| D3E8 (I82K, T126V) | 27 | I82K, T126V | | 2500 |
| D3E8-KE (D3E8 (I82K, R222E)) | 28 | I82K, R222E | | 63 |

Example 6: Treatment of Non-Small-Cell Lung Cancer Cells with Polypeptide

In order to evaluate the biological activities of the repebodies having increased binding affinities, the inhibitory effects of the repebodies on the activity of IL-6 were examined.

Example 6-1: Culture of Non-Small-Cell Lung Cancer Cells

First, a human non-small-cell lung cancer (H1650) cell line was suspended in medium [RPMI (Gibco-BRL, Grand Island, N.Y., USA) with 10% fetal bovine serum (Gibco-BRL), sodium pyruvate, nonessential amino acids, penicillin G (100 IU/ml) 및 streptomycin (100 mg/ml)] at a concentration of 1×10⁵ cells/ml and cultured in a 100-pi cell culture dish under the conditions of 37° C. and 5% $CO_2$.

Example 6-2: Treatment with Polypeptide (Repebody)

To the non-small-cell lung cancer cell medium prepared in Example 2-1, repebody-D3E8 (I82K) (SEQ ID NO: 22)

and repebody-D3E8-KE (SEQ ID NO: 28), selected in Example 1-3, and repebody-D3E8C4 (SEQ ID NO: 15), repebody-D3E8 (SEQ ID NO: 9) and repebody-D3 (SEQ ID NO: 5), selected by the present inventors in the previous patent and having the ability to bind to interleukin-6, were added at concentrations of 0.1, 1 and 10 mg/ml. As controls, an anti-interleukin-6 monoclonal antibody and an isotype control were added at a concentration of 1 mg/ml, and the cell medium was incubated for 18 hours.

Example 7: Analysis of Effects of Repebody on STAT3 and Interleukin-6

The medium of the non-small-cell lung cancer cells treated with the repebody in Example 6-2 were collected, and an enzyme immunoassay for interleukin-6 in the collected medium was performed. The cells were collected, and Western blot analysis for STAT3 in the collected cells was performed. The results of the analysis are shown in FIG. 12.

Figure 12:
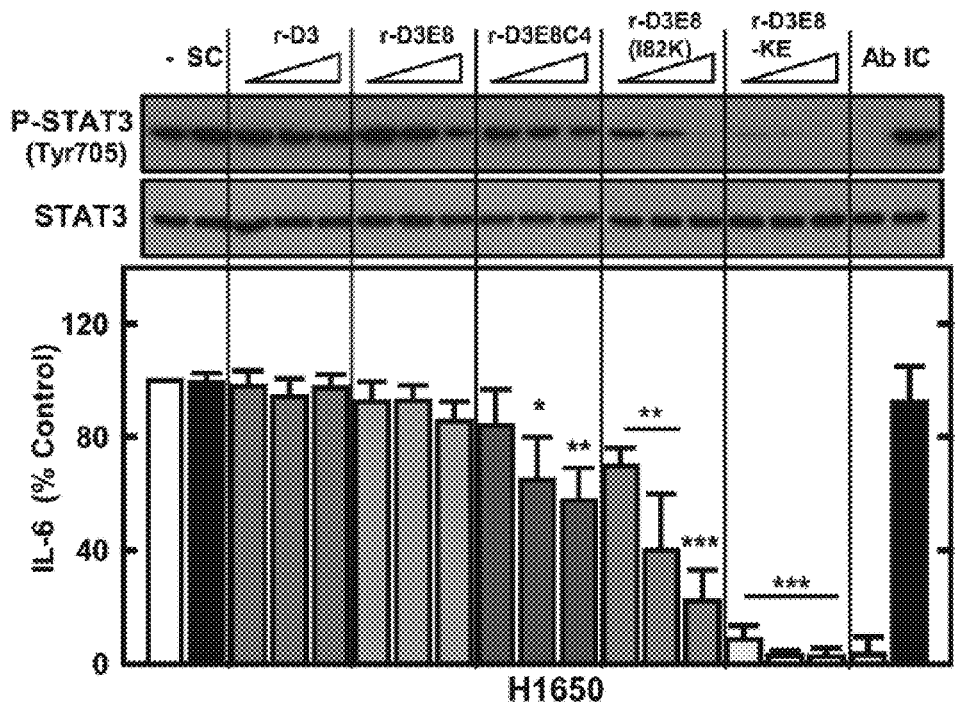
FIG. 12 is a graphic diagram showing the results obtained by treating a medium of non-small-cell lung cancer cells with peptides (D3, D3E8, D3E8C4, D3E8 (I82K), and D3E8-KE) and measuring changes in STAT3 activity and interleukin-6 production.

As can be seen in FIG. 12, the intracellular STAT3 activity (P-STAT3) and the production of interleukin-6 were significantly decreased by treatment with the repebody in a concentration-dependent manner. Particularly, it could be seen that D3E8 (I82K) (SEQ ID NO: 22) and D3E8-KE (SEQ ID NO: 28), selected in the present invention, had excellent effects on the inhibition of intracellular STAT3 activity and interleukin-6 production compared to other repebodies (D3 and D3E8), and among them, D3E8-KE (SEQ ID NO: 28) showed inhibitory abilities similar to those of the control anti-interleukin-6 monoclonal antibody.

Example 8: Analysis of Effect of Repebody on Cell Viability

Figure 13:
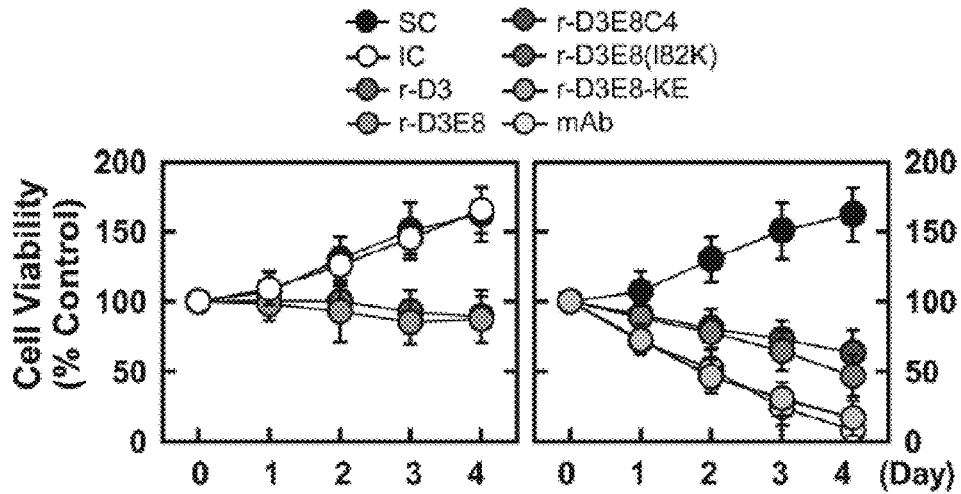
FIG. 13 is a graphic diagram showing the results obtained by treating non-small-cell lung cancer cells with repebodies (D3, D3E8, D3E8C4, D3E8 (I82K), and D3E8-KE), and then subjecting the cells to an MTT assay to measure cell viability.

For the non-small-cell lung cancer cells treated with each of the polypeptides and the controls at a concentration of 1 mg/ml in Example 6-2, an MTT assay was performed to determine the viability of the cells. The medium of the non-small-cell lung cancer cells treated with each of the polypeptides and the controls at 1-day intervals for a total of 4 days was removed, and then the cells were incubated with an MTT tetrazolium solution for 4 hours. The solution was removed, and then DMSO was added and reacted with the cells for 15-20 minutes, after which the absorbance at a wavelength of 540 nm was measured using an ELISA reader. The results of the measurement are shown in FIG. 13.

As a result, it could be seen that the viability of the cells was lower in the order of D3, D3E8, D3E8C4, D3E8 (I82K) and D3E8-KE. Among them, repebody D3E8-KE (SEQ ID NO: 28) showed a cell killing ability similar to that of the control anti-interleukin-6 monoclonal antibody. In other words, from the results in FIGS. 12 and 13, it could be seen that the cell death of the non-small-cell lung cancer cells was induced by treatment with the polypeptides of the present invention.

Figure 14:
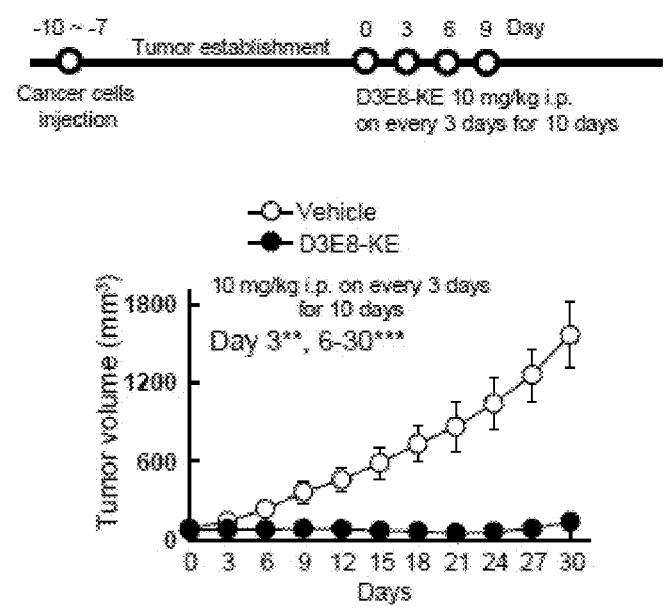
FIG. 14 is a graphic diagram showing the results obtained by intraperitoneally injecting a polypeptide (D3E8-KE) and a control (PBS) four times at 3-day intervals for 10 days into xenograft mice injected with non-small-cell lung cancer cells, and then measuring a change in the tumor volume.

Example 9: Analysis of Effect of Repebody on Xenograft Mouse Model $5 \times 10^6$ non-small-cell lung cancer cells were injected subcutaneously into the right side of nude mice to construct xenograft mouse models. Then, repebody D3E8-KE (SEQ ID NO: 28) was injected intraperitoneally into the mouse models at a dose of 10 mg/kg, four times at 3-day intervals for 10 days. As a control, PBS was used. The volume of the tumor was measured at 3-day intervals and calculated according to the following equation: tumor volume= (length×width$^2$)/2. The results of the calculation are shown in FIG. 14. As a result, it could be seen that the volume of the tumor in the group treated with D3E8-KE (SEQ ID NO: 28) significantly decreased.

Figure 15:
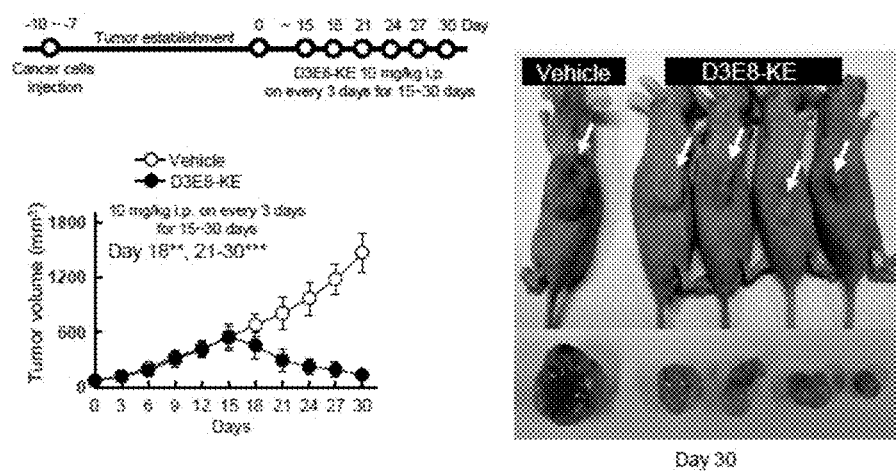
FIG. 15 is a graphic diagram showing the results obtained by intraperitoneally injecting repebody (D3E8-KE) and a control (PBS) five times at 3-day intervals for 15 days into xenograft mice injected with non-small-cell lung cancer cells, and then measuring a change in the tumor volume.

Meanwhile, xenograft mouse models injected with non-small-cell lung cancer cells were treated with the repebody, and the tumor inhibitory activity of the repebody was analyzed to evaluate the effect of the polypeptide on tumors. Specifically, tumors were allowed to grow actively for 15 days, and then D3E8-KE (SEQ ID NO: 28) was injected intraperitoneally at a concentration of 10 mg/kg, five times at 3-day intervals for 15 days. As a control, PBS was used. The tumor volume was measured at 3-day intervals, and the results of the measurement are shown in FIG. 15. As can be seen in FIG. 15, the volume of the actively growing tumor was significantly decreased by treatment with D3E8-KE (SEQ ID NO: 28).

INDUSTRIAL APPLICABILITY

The repebody of the present invention can bind to IL-6 with an affinity higher than that of naturally occurring IL-6 receptor (IL-6Ra) to significantly reduce the activity of STAT3 and the concentration of interleukin-6, and thus can be widely used for the development of agents for preventing or treating IL-6-related diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A repebody capable of binding to interleukin-6 (IL-6), said repebody comprising an amino acid sequence selected from the group consisting of SEQ ID NOs: 9 and 11 to 28.

2. The repebody of claim 1, wherein the repebody is capable of inhibiting the activity of the interleukin-6.

3. A composition for treating non-small cell lung cancer, which contains the repebody of claim 1 as an active ingredient.

4. A polynucleotide encoding the repebody of claim 1.

5. A vector comprising the polynucleotide of claim 4.

6. A recombinant microorganism having introduced therein the polynucleotide of claim 4 and a vector comprising said polynucleotide.

7. A method for producing a repebody binding to interleukin-6, wherein the method comprises:
   (i) expressing the repebody by culturing the recombinant microorganism of claim 6; and
   (ii) recovering the expressed repebody.

* * * * *

SEQUENCE LISTING

```
<160> NUMBER OF SEQ ID NOS: 68

<210> SEQ ID NO 1
<211> LENGTH: 798
<212> TYPE: DNA
<213> ORGANISM: Artificial
<220> FEATURE:
<223> OTHER INFORMATION: Repebody-Library
<220> FEATURE:
<221> NAME/KEY: misc_feature
<222> LOCATION: (271)..(272)
<223> OTHER INFORMATION: n is a, c, g, or t
<220> FEATURE:
<221> NAME/KEY: misc_feature
<222> LOCATION: (277)..(278)
```

```
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (343)..(344)
<223> OTHER INFORMATION: n is a, c, g, or t
<220> FEATURE:
<221> NAME/KEY: misc_feature
<222> LOCATION: (349)..(350)
<223> OTHER INFORMATION: n is a, c, g, or t
<220> FEATURE:
<221> NAME/KEY: misc_feature
<222> LOCATION: (352)..(353)
<223> OTHER INFORMATION: n is a, c, g, or t

<400> SEQUENCE: 1
gaaaccatta ccgtgagcac cccgatcaaa cagattttc cggatgacgc gttcgccgaa      60
acgatcaaag caaacctgaa gaaaagagc gttaccgatg ctgtcacgca aaatgaactg     120
aacagtattg accagatcat tgcgaataac tccgatatca aatcagtgca aggcattcag    180
tatctgccga atgttcgtta cctggccctg ggtggcaaca aactgcatga catctcggca    240
ctgaaagaac tgaccaatct gacgtatctg nnkctgnnkn nkaaccaact gcagagcctg    300
ccgaacggcg tgtttgataa actgacgaac ctgaaagaac tgnnkctgnn knnkaatcaa    360
ctgcagtctc tgccggatgg tgtgttcgac aaactgacca acctgacgta cctgaatctg    420
gctcacaacc aactgcagag tctgccgaaa ggcgtgtttg acaaactgac caatctgacg    480
gaactggatc tgtcctataa ccaactgcag tcactgccgg aaggtgtttt cgacaaactg    540
acccagctga agatctgcg cctgtaccag aatcagctga atcggtccc ggacggcgtg     600 tttgatcgtc tgaccagcct gcagtatatc tggctgcatg ataacccgtg ggattgcacc    660
tgtccgggta ttcgctacct gtctgaatgg atcaataaac acagtggcgt tgtccgtaac    720
tccgcgggtt cagttgcccc ggattcggcg aaatgctccg cagcggtaa accggtgcgt     780 agcattattt gcccgacc                                                  798

<210> SEQ ID NO 2
<211> LENGTH: 4615
<212> TYPE: DNA
<213> ORGANISM: Artificial
<220> FEATURE:
<223> OTHER INFORMATION: pBEL118N
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (710)..(711)
<223> OTHER INFORMATION: n is a, c, g, or t
<220> FEATURE:
<221> NAME/KEY: misc_feature
<222> LOCATION: (713)..(714)
<223> OTHER INFORMATION: n is a, c, g, or t
<220> FEATURE:
<221> NAME/KEY: misc_feature
<222> LOCATION: (776)..(777)
<223> OTHER INFORMATION: n is a, c, g, or t
<220> FEATURE:
<221> NAME/KEY: misc_feature
<222> LOCATION: (782)..(783)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
```

<400> SEQUENCE: 2

```
acatgttctt tcctgcgtta tcccctgatt ctgtggataa ccgtattacc gcctttgagt      60
gagctgatac cgctcgccgc agccgaacga ccgagcgcag cgagtcagtg agcgaggaag     120
cggaagagcg cccaatacgc aaaccgcctc tccccgcgcg ttggccgatt cattaatgca     180
gctggcacga caggtttccc gactggaaag cgggcagtga gcgcaacgca attaatgtga     240
gttagctcac tcattaggca ccccaggctt tacactttat gcttccggct cgtatgttgt     300
gtggaattgt gagcggataa caatttcaca caggaaacag accatggcca tgaaaataaa     360
aacaggtgca cgcatcctcg cattatccgc attaacgacg atgatgtttt ccgcctcggc     420
tctcgccgaa ttcgaaacca ttaccgtgag cacccccgatc aaacagattt ttccggatga     480
cgcgttcgcc gaaacgatca agcaaacct gaagaaaaag agcgttaccg atgctgtcac     540
gcaaaatgaa ctgaacagta ttgaccagat cattgcgaat aactccgata tcaaatcagt     600
gcaaggcatt cagtatctgc gaatgttcg ttacctggcc ctgggtggca caaaactgca     660
tgacatctcg gcactgaaag aactgaccaa tctgacgtat ctgnnkctgn nknnkaacca     720
actgcagagc ctgccgaacg gcgtgtttga taaactgacg aacctgaaag aactgnnkct     780
gnnknnkaat caactgcagt ctctgccgga tggtgtgttc gacaaactga ccaacctgac     840
gtacctgaat ctggctcaca accaactgca gagtctgccg aaaggcgtgt ttgacaaact     900
gaccaatctg acggaactgg atctgtccta taaccaactg cagtcactgc cggaaggtgt     960
tttcgacaaa ctgacccagc tgaaagatct cgcctgtac cagaatcagc tgaaatcggt    1020
cccggacggc gtgtttgatc gtctgaccag cctgcagtat atctggctgc atgataaccc    1080
gtgggattgc acctgtccgg gtattcgcta cctgtctgaa tggatcaata acacagtgg    1140
cgttgtccgt aactccgcgg gttcagttgc cccggattcg gcgaaatgct ccggcagcgg    1200
taaaccggtg cgtagcatta tttgcccgac ctcgagcacc accaccacca ccactagggc    1260
ggcggctctg gtggtggttc tggtggcggc tctgagggtg gtggctctga gggtggcggt    1320
tctgagggtg gcggctctga gggaggcggt tccggtggtg gctctggttc cggtgatttt    1380
gattatgaaa agatggcaaa cgctaataag ggggctatga ccgaaaatgc cgatgaaaac    1440
gcgctacagt ctgacgctaa aggcaaactt gattctgtcg ctactgatta cggtgctgct    1500
atcgatggtt tcattggtga cgtttccggc cttgctaatg gtaatggtgc tactggtgat    1560
tttgctggct ctaattccca aatggctcaa gtcggtgacg gtgataattc acctttaatg    1620
aataatttcc gtcaatattt accttccctc cctcaatcgg ttgaatgtcg cccttttgtc    1680
tttggcgctg gtaaaccata tgaattttct attgattgtg acaaaataaa cttattccgt    1740
ggtgtctttg cgtttctttt atatgttgcc acctttatgt atgtatttc tacgtttgct    1800
aacatactgc gtaataagga gtcttagtaa ggatcctcta gagtcgacct gcaggcatgc    1860
aagcttggca ctggccgtcg ttttacaacg tcgtgactgg gaaaaccctg gcgttaccca    1920
acttaatcgc cttgcagcac atccccctt cgccagctgg cgtaatagcg aagaggcccg    1980
caccgatcgc ccttcccaac agttgcgcag cctgaatggc gaatggcgtc taagaaacca    2040
ttattatcat gacattaacc tataaaaata ggcgtatcac gaggcccttt cgtctcgcgc    2100
gtttcggtga tgacggtgaa aacctctgac acatgcagct cccggagacg gtcacagctt    2160
gtctgtaagc ggatgccggg agcagacaag cccgtcaggg cgcgtcagcg ggtgttggcg    2220
ggtgtcgggg ctggcttaac tatgcggcat cagagcagat tgtactgaga gtgcaccata    2280
```

```
aaattgtaaa cgttaatatt tgttaaaat tcgcgttaaa tttttgttaa atcagctcat      2340 ttttaacca ataggccgaa atcggcaaaa tcccttataa atcaaaagaa tagcccgaga      2400
tagggttgag tgttgttcca gtttggaaca agagtccact attaaagaac gtggactcca    2460
acgtcaaagg gcgaaaaacc gtctatcagg gcgatggccc actacgtgaa ccatcaccca    2520
aatcaagttt tttggggtcg aggtgccgta aagcactaaa tcggaaccct aaagggagcc    2580
cccgatttag agcttgacgg ggaaagccgg cgaacgtggc gagaaaggaa gggaagaaag    2640
cgaaaggagc gggcgctagg gcgctggcaa gtgtagcggt cacgctgcgc gtaaccacca    2700
cacccgccgc gcttaatgcg ccgctacagg gcgcgtacta tggttgcttt gacgtatgcg    2760
gtgtgaaata ccgcacagat gcgtaaggag aaaataccgc atcaggcgtc aggtggcact    2820
tttcggggaa atgtgcgcgg aaccctatt tgtttatttt tctaaataca ttcaaatatg     2880
tatccgctca tgagacaata accctgataa atgcttcaat aatattgaaa aagaagagt     2940 atgagtattc aacatttccg tgtcgccctt attccctttt tgcggcatt ttgccttcct    3000 gttttgctc acccagaaac gctggtgaaa gtaaaagatg ctgaagatca gttgggtgca    3060
cgagtgggtt acatcgaact ggatctcaac agcggtaaga tccttgagag ttttcgcccc    3120
gaagaacgtt ttccaatgat gagcactttt aaagttctgc tatgtggcgc ggtattatcc    3180
cgtattgacg ccgggcaaga gcaactcggt cgccgcatac actattctca gaatgacttg    3240
gttgagtact caccagtcac agaaaagcat cttacggatg gcatgacagt aagagaatta    3300
tgcagtgctg ccataaccat gagtgataac actgcggcca acttacttct gacaacgatc    3360
ggaggaccga aggagctaac cgcttttttg cacaacatgg gggatcatgt aactcgcctt    3420
gatcgttggg aaccggagct gaatgaagcc ataccaaacg acgagcgtga ccacgatg     3480 cctgtagcaa tggcaacaac gttgcgcaaa ctattaactg gcgaactact tactctagct    3540
tcccggcaac aattaataga ctggatggag gcggataaag ttgcaggacc acttctgcgc    3600
tcggcccttc cggctggctg gtttattgct gataaatctg gagccggtga gcgtgggtct    3660
cgcggtatca ttgcagcact ggggccagat ggtaagccct cccgtatcgt agttatctac    3720
acgacgggga gtcaggcaac tatggatgaa cgaaatagac agatcgctga gataggtgcc    3780
tcactgatta agcattggta actgtcagac caagtttact catatatact ttagattgat    3840
ttaaaacttc atttttaatt taaaaggatc taggtgaaga tcctttttga atctcatg     3900 accaaaatcc cttaacgtga gttttcgttc cactgagcgt cagaccccgt agaaaagatc    3960
aaaggatctt cttgagatcc ttttttcctg cgcgtaatct gctgcttgca acaaaaaaa    4020 ccaccgctac cagcggtggt ttgtttgccg gatcaagagc taccaactct ttttccgaag    4080
gtaactggct tcagcagagc gcagatacca aatactgtcc ttctagtgta gccgtagtta    4140
ggccaccact tcaagaactc tgtagcaccg cctacatacc tcgctctgct aatcctgtta    4200
ccagtggctg ctgccagtgg cgataagtcg tgtcttaccg ggttggactc aagacgatag    4260
ttaccggata aggcgcagcg gtcgggctga acggggggtt cgtgcacaca gcccagcttg    4320
gagcgaacga cctacaccga actgagatac ctacagcgtg agctatgaga aagcgccacg    4380
cttcccgaag ggagaaaggc ggacaggtat ccggtaagcg gcagggtcgg aacaggagag    4440
cgcacgaggg agcttccagg gggaaacgcc tggtatcttt atagtcctgt cgggtttcgc    4500
cacctctgac ttgagcgtcg atttttgtga tgctcgtcag ggggcggag cctatggaaa     4560 aacgccagca acgcggcctt tttacggttc ctggccttttt gctggccttt tgctc        4615
```

```
<210> SEQ ID NO 3
<211> LENGTH: 266
<212> TYPE: PRT
<213> ORGANISM: Artificial
<220> FEATURE:
<223> OTHER INFORMATION: Repebody-B3

<400> SEQUENCE: 3

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Val Leu Glu Pro Asn Gln
                85                  90                  95

Leu Gln Ser Leu Pro Asn Gly Val Phe Asp Lys Leu Thr Asn Leu Lys
            100                 105                 110

Glu Leu Ala Leu Trp Ile Asn Gln Leu Gln Ser Leu Pro Asp Gly Val
        115                 120                 125

Phe Asp Lys Leu Thr Asn Leu Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 4
<211> LENGTH: 266
<212> TYPE: PRT
<213> ORGANISM: Artificial
<220> FEATURE:
<223> OTHER INFORMATION: Repebody-C8

<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45
```

```
Asn Asn Ser Asp Ile Lys Ser Val Gln Gly Ile Gln Tyr Leu Pro Asn
         50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Val Leu Glu Pro Asn Gln
                     85                  90                  95

Leu Gln Ile Leu Pro Asn Gly Val Phe Asp Lys Leu Thr Asn Leu Lys
                100                 105                 110

Glu Leu Ala Leu Trp Leu Asn Gln Leu Gln Ser Leu Pro Asp Gly Val
            115                 120                 125

Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 5
<211> LENGTH: 266
<212> TYPE: PRT
<213> ORGANISM: Artificial
<220> FEATURE:
<223> OTHER INFORMATION: Repebody-D3

<400> SEQUENCE: 5

Glu Thr Ile Thr Val Ser Thr Pro Ile Lys Gln Ile Phe Pro Asp Asp
 1                   5                  10                  15

Ala Phe Ala Glu Thr Ile Lys Ala Asn Leu Lys Lys Lys Ser Val Thr
                 20                  25                  30

Asp Ala Val Thr Gln Asn Glu Leu Asn Ser Ile Asp Gln Ile Ile Ala
             35                  40                  45

Asn Asn Ser Asp Ile Lys Ser Val Gln Gly Ile Gln Tyr Leu Pro Asn
         50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Val Leu Glu Pro Asn Gln
                     85                  90                  95

Leu Gln Ile Leu Pro Asn Gly Val Phe Asp Lys Leu Thr Asn Leu Lys
                100                 105                 110

Glu Leu Ala Leu Trp Leu Asn Gln Leu Gln Ser Leu Pro Asp Gly Val
            115                 120                 125

Phe Asp Lys Leu Thr Asn Leu Thr Tyr Leu Asn Leu Ala His Asn Gln
        130                 135                 140
```

```
Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
                210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
                260                 265

<210> SEQ ID NO 6
<211> LENGTH: 266
<212> TYPE: PRT
<213> ORGANISM: Artificial
<220> FEATURE:
<223> OTHER INFORMATION: Repebody-F11

<400> SEQUENCE: 6

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
                35                  40                  45

Asn Asn Ser Asp Ile Lys Ser Val Gln Gly Ile Gln Tyr Leu Pro Asn
                50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Val Leu Glu Pro Asn Gln
                85                  90                  95

Leu Gln Ile Leu Pro Asn Gly Val Phe Asp Lys Leu Thr Asn Leu Lys
                100                 105                 110

Glu Leu Ala Leu Trp Leu Asn Gln Leu Gln Ser Leu Pro Asp Gly Val
                115                 120                 125

Phe Asp Lys Leu Thr Asn Leu Thr Tyr Leu Asn Leu Ala His Asn Gln
                130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
                210                 215                 220

Arg Tyr Leu Ser Glu Trp Ile Asn Lys His Ser Gly Val Val Arg Asn
225                 230                 235                 240
```

```
Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 7
<211> LENGTH: 266
<212> TYPE: PRT
<213> ORGANISM: Artificial
<220> FEATURE:
<223> OTHER INFORMATION: Repebody-MD2

<400> SEQUENCE: 7

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
            115                 120                 125

Phe Asp Lys Leu Thr Asn Leu Thr Tyr Leu Asn Leu Ala His Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 8
<211> LENGTH: 266
<212> TYPE: PRT
<213> ORGANISM: Artificial
<220> FEATURE:
<223> OTHER INFORMATION: Repebody-D3E5

<400> SEQUENCE: 8

Glu Thr Ile Thr Val Ser Thr Pro Ile Lys Gln Ile Phe Pro Asp Asp
1               5                   10                  15
```

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Met Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 9
<211> LENGTH: 266
<212> TYPE: PRT
<213> ORGANISM: Artificial
<220> FEATURE:
<223> OTHER INFORMATION: Repebody-D3E8

<400> SEQUENCE: 9

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

```
Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
            165                 170                 175

Phe Asp Lys Leu Thr Gln Leu Lys Asp Leu Arg Leu Tyr Gln Asn Gln
        180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 10
<211> LENGTH: 266
<212> TYPE: PRT
<213> ORGANISM: Artificial
<220> FEATURE:
<223> OTHER INFORMATION: Repebody-D3E10

<400> SEQUENCE: 10

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
            85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
            115                 120                 125

Phe Asp Lys Leu Ile Asn Leu Thr Tyr Leu Asn Leu Ala Trp Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
            165                 170                 175

Phe Asp Lys Leu Thr Gln Leu Lys Asp Leu Arg Leu Tyr Gln Asn Gln
        180                 185                 190

Leu Lys Ser Val Pro Asp Gly Val Phe Asp Arg Leu Thr Ser Leu Gln
            195                 200                 205
```

Tyr Ile Trp Leu His Asp Asn Pro Trp Asp Cys Thr Cys Pro Gly Ile
         210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 11
<211> LENGTH: 266
<212> TYPE: PRT
<213> ORGANISM: Artificial
<220> FEATURE:
<223> OTHER INFORMATION: Repebody-D3E8B2

<400> SEQUENCE: 11

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Thr Leu Val Gln Asn Lys Leu His Asp Ile Ser Ala
65                  70                  75                  80

Leu Lys Glu Leu Thr Asn Leu Thr Tyr Leu Thr Leu Glu Ser Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
         210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 12
<211> LENGTH: 266
<212> TYPE: PRT
<213> ORGANISM: Artificial

<220> FEATURE:
<223> OTHER INFORMATION: Repebody-D3E8B3

<400> SEQUENCE: 12

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Thr Leu Gln Ser Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 13
<211> LENGTH: 266
<212> TYPE: PRT
<213> ORGANISM: Artificial
<220> FEATURE:
<223> OTHER INFORMATION: Repebody-D3E8B4

<400> SEQUENCE: 13

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Thr Leu Thr Asn Asn Lys Leu His Asp Ile Ser Ala

-continued

```
                65                  70                  75                  80
Leu Lys Glu Leu Thr Asn Leu Thr Tyr Leu Thr Leu Glu Pro Asn Gln
                    85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
                260                 265

<210> SEQ ID NO 14
<211> LENGTH: 266
<212> TYPE: PRT
<213> ORGANISM: Artificial
<220> FEATURE:
<223> OTHER INFORMATION: Repebody-D3E8B8

<400> SEQUENCE: 14

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Thr Leu Arg Asn Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
```

```
                        165                 170                 175
Phe Asp Lys Leu Thr Gln Leu Lys Asp Leu Arg Leu Tyr Gln Asn Gln
                    180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
                260                 265

<210> SEQ ID NO 15
<211> LENGTH: 266
<212> TYPE: PRT
<213> ORGANISM: Artificial
<220> FEATURE:
<223> OTHER INFORMATION: Repebody-D3E8C4

<400> SEQUENCE: 15

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Lys Leu Thr Leu Val Ser Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
```

<210> SEQ ID NO 16
<211> LENGTH: 266
<212> TYPE: PRT
<213> ORGANISM: Artificial
<220> FEATURE:
<223> OTHER INFORMATION: Repebody-D3E8C7

<400> SEQUENCE: 16

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Thr Leu Ile Thr Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 17
<211> LENGTH: 266
<212> TYPE: PRT
<213> ORGANISM: Artificial
<220> FEATURE:
<223> OTHER INFORMATION: Repebody-D3E8C9

<400> SEQUENCE: 17

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

-continued

```
Asp Ala Val Thr Gln Asn Glu Leu Asn Ser Ile Asp Gln Ile Ile Ala
             35                  40                  45

Asn Asn Ser Asp Ile Lys Ser Val Gln Gly Ile Gln Tyr Leu Pro Asn
 50                  55                  60

Val Arg Tyr Leu Ala Leu Ser Ser Asn Lys Leu His Asp Ile Ser Ala
 65                  70                  75                  80

Leu Lys Glu Leu Thr Asn Leu Thr Tyr Leu Thr Leu Glu Pro Asn Gln
                 85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 18
<211> LENGTH: 266
<212> TYPE: PRT
<213> ORGANISM: Artificial
<220> FEATURE:
<223> OTHER INFORMATION: Repebody-D3E8C11

<400> SEQUENCE: 18

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
                 20                  25                  30

Asp Ala Val Thr Gln Asn Glu Leu Asn Ser Ile Asp Gln Ile Ile Ala
             35                  40                  45

Asn Asn Ser Asp Ile Lys Ser Val Gln Gly Ile Gln Tyr Leu Pro Asn
 50                  55                  60

Val Arg Tyr Leu Ser Leu Ile Asn Asn Lys Leu His Asp Ile Ser Ala
 65                  70                  75                  80

Leu Lys Glu Leu Thr Asn Leu Thr Tyr Leu Thr Leu Glu Pro Asn Gln
                 85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
            115                 120                 125
```

```
Phe Asp Lys Leu Thr Asn Leu Thr Tyr Leu Asn Leu Ala Phe Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 19
<211> LENGTH: 266
<212> TYPE: PRT
<213> ORGANISM: Artificial
<220> FEATURE:
<223> OTHER INFORMATION: Repebody-D3E8H2

<400> SEQUENCE: 19

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
50                  55                  60

Val Arg Tyr Leu Leu Arg Ser Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220
```

```
Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 20
<211> LENGTH: 266
<212> TYPE: PRT
<213> ORGANISM: Artificial
<220> FEATURE:
<223> OTHER INFORMATION: Repebody-D3E8H3

<400> SEQUENCE: 20

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
50                  55                  60

Val Arg Met Leu Ile Leu Arg Ser Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 21
<211> LENGTH: 266
<212> TYPE: PRT
<213> ORGANISM: Artificial
<220> FEATURE:
<223> OTHER INFORMATION: Repebody-D3E8H5

<400> SEQUENCE: 21
```

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
                35                  40                  45

Asn Asn Ser Asp Ile Lys Ser Val Gln Gly Ile Gln Tyr Leu Pro Asn
        50                  55                  60

Val Arg Val Leu Met Leu Arg Ser Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Val Gly Val
            115                 120                 125

Phe Asp Lys Leu Thr Asn Leu Thr Tyr Leu Asn Leu Ala Phe Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 22
<211> LENGTH: 266
<212> TYPE: PRT
<213> ORGANISM: Artificial
<220> FEATURE:
<223> OTHER INFORMATION: Repebody-D3E8(I82K)

<400> SEQUENCE: 22

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Lys Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95
```

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 23
<211> LENGTH: 266
<212> TYPE: PRT
<213> ORGANISM: Artificial
<220> FEATURE:
<223> OTHER INFORMATION: Repebody-D3E8(N84K)

<400> SEQUENCE: 23

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Lys Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

```
Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 24
<211> LENGTH: 266
<212> TYPE: PRT
<213> ORGANISM: Artificial
<220> FEATURE:
<223> OTHER INFORMATION: Repebody-D3E8(T126V)

<400> SEQUENCE: 24

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Val Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 25
```

```
<211> LENGTH: 266
<212> TYPE: PRT
<213> ORGANISM: Artificial
<220> FEATURE:
<223> OTHER INFORMATION: Repebody-D3E8(R222E)

<400> SEQUENCE: 25

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
            100                 105                 110

Glu Leu Gln Leu Trp Ala Asn Gln Leu Gln Ser Leu Pro Asp Gly Val
        115                 120                 125

Phe Asp Lys Leu Thr Asn Leu Thr Tyr Leu Asn Leu Ala Phe Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Glu Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 26
<211> LENGTH: 266
<212> TYPE: PRT
<213> ORGANISM: Artificial
<220> FEATURE:
<223> OTHER INFORMATION: Repebody-D3E8(Y244E)

<400> SEQUENCE: 26

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
```

50                  55                  60
Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Thr Leu Glu Pro Asn Gln
                    85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
                115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Glu Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
                260                 265

<210> SEQ ID NO 27
<211> LENGTH: 266
<212> TYPE: PRT
<213> ORGANISM: Artificial
<220> FEATURE:
<223> OTHER INFORMATION: Repebody-D3E8(I82K, T126V)

<400> SEQUENCE: 27

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Lys Ala
                35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Val Leu Glu Pro Asn Gln
                85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
                115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr

```
                 145                 150                 155                 160
Glu Leu Asp Leu Ser Tyr Asn Gln Leu Gln Ser Leu Pro Lys Gly Val
                 165                 170                 175

Phe Asp Lys Leu Thr Gln Leu Lys Asp Leu Arg Leu Tyr Gln Asn Gln
                 180                 185                 190

Leu Lys Ser Val Pro Asp Gly Val Phe Asp Arg Leu Thr Ser Leu Gln
                 195                 200                 205

Tyr Ile Trp Leu His Asp Asn Pro Trp Asp Cys Thr Cys Pro Gly Ile
                 210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                 245                 250                 255

Lys Pro Val Arg Ser Ile Ile Cys Pro Thr
                 260                 265

<210> SEQ ID NO 28
<211> LENGTH: 266
<212> TYPE: PRT
<213> ORGANISM: Artificial
<220> FEATURE:
<223> OTHER INFORMATION: Repebody-D3E8-KE, D3E8(I82K, R222E)

<400> SEQUENCE: 28

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Lys Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Thr Leu Glu Pro Asn Gln
                85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
                115                 120                 125

Phe Asp Lys Leu Thr Asn Leu Thr Tyr Leu Asn Leu Ala Phe Asn Gln
                130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Glu Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
                210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
```

```
                    245                 250                 255

Lys Pro Val Arg Ser Ile Ile Cys Pro Thr
            260                 265

<210> SEQ ID NO 29
<211> LENGTH: 39
<212> TYPE: PRT
<213> ORGANISM: Artificial
<220> FEATURE:
<223> OTHER INFORMATION: partial N-terminal fragment of Internalin
      protein

<400> SEQUENCE: 29

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu
        35

<210> SEQ ID NO 30
<211> LENGTH: 83
<212> TYPE: PRT
<213> ORGANISM: Artificial
<220> FEATURE:
<223> OTHER INFORMATION: N-terminal of Internalin B
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid

<400> SEQUENCE: 30

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Xaa
    50                  55                  60
```

```
Leu Xaa Xaa Leu Xaa Leu Xaa Xaa Asn Xaa Ile Xaa Asp Ile Xaa Xaa
65                  70                  75                  80

Leu Xaa Xaa

<210> SEQ ID NO 31
<211> LENGTH: 83
<212> TYPE: PRT
<213> ORGANISM: Artificial
<220> FEATURE:
<223> OTHER INFORMATION: N-terminal of Internalin protein

<400> SEQUENCE: 31

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu

<210> SEQ ID NO 32
<211> LENGTH: 83
<212> TYPE: PRT
<213> ORGANISM: Artificial
<220> FEATURE:
<223> OTHER INFORMATION: N-terminal of Internalin protein

<400> SEQUENCE: 32

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Thr Leu Val Gln Asn Lys Leu His Asp Ile Ser Ala
65                  70                  75                  80

Leu Lys Glu

<210> SEQ ID NO 33
<211> LENGTH: 83
<212> TYPE: PRT
<213> ORGANISM: Artificial
<220> FEATURE:
<223> OTHER INFORMATION: N-terminal of Internalin protein

<400> SEQUENCE: 33

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
```

```
                    50                  55                  60
Val Arg Tyr Leu Thr Leu Thr Asn Asn Lys Leu His Asp Ile Ser Ala
 65                  70                  75                  80

Leu Lys Glu

<210> SEQ ID NO 34
<211> LENGTH: 83
<212> TYPE: PRT
<213> ORGANISM: Artificial
<220> FEATURE:
<223> OTHER INFORMATION: N-terminal of Internalin protein

<400> SEQUENCE: 34

Glu Thr Ile Thr Val Ser Thr Pro Ile Lys Gln Ile Phe Pro Asp Asp
 1                   5                  10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
         50                  55                  60

Val Arg Tyr Leu Thr Leu Arg Asn Asn Lys Leu His Asp Ile Ser Ala
 65                  70                  75                  80

Leu Lys Glu

<210> SEQ ID NO 35
<211> LENGTH: 83
<212> TYPE: PRT
<213> ORGANISM: Artificial
<220> FEATURE:
<223> OTHER INFORMATION: N-terminal of Internalin protein

<400> SEQUENCE: 35

Glu Thr Ile Thr Val Ser Thr Pro Ile Lys Gln Ile Phe Pro Asp Asp
 1                   5                  10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
         50                  55                  60

Val Arg Tyr Leu Thr Leu Arg Asn Asn Lys Leu His Asp Ile Ser Ala
 65                  70                  75                  80

Leu Lys Glu

<210> SEQ ID NO 36
<211> LENGTH: 83
<212> TYPE: PRT
<213> ORGANISM: Artificial
<220> FEATURE:
<223> OTHER INFORMATION: N-terminal of Internalin protein

<400> SEQUENCE: 36

Glu Thr Ile Thr Val Ser Thr Pro Ile Lys Gln Ile Phe Pro Asp Asp
 1                   5                  10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45
```

Asn Asn Ser Asp Ile Lys Ser Val Gln Gly Ile Gln Tyr Leu Pro Asn
            50                  55                  60

Val Arg Lys Leu Thr Leu Val Ser Asn Lys Leu His Asp Ile Ser Ala
65                  70                  75                  80

Leu Lys Glu

<210> SEQ ID NO 37
<211> LENGTH: 83
<212> TYPE: PRT
<213> ORGANISM: Artificial
<220> FEATURE:
<223> OTHER INFORMATION: N-terminal of Internalin protein

<400> SEQUENCE: 37

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
            50                  55                  60

Val Arg Tyr Leu Thr Leu Ile Thr Asn Lys Leu His Asp Ile Ser Ala
65                  70                  75                  80

Leu Lys Glu

<210> SEQ ID NO 38
<211> LENGTH: 83
<212> TYPE: PRT
<213> ORGANISM: Artificial
<220> FEATURE:
<223> OTHER INFORMATION: N-terminal of Internalin protein

<400> SEQUENCE: 38

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
            50                  55                  60

Val Arg Tyr Leu Ala Leu Ser Ser Asn Lys Leu His Asp Ile Ser Ala
65                  70                  75                  80

Leu Lys Glu

<210> SEQ ID NO 39
<211> LENGTH: 83
<212> TYPE: PRT
<213> ORGANISM: Artificial
<220> FEATURE:
<223> OTHER INFORMATION: N-terminal of Internalin protein

<400> SEQUENCE: 39

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

```
Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
 50                  55                  60

Val Arg Tyr Leu Ser Leu Ile Asn Asn Lys Leu His Asp Ile Ser Ala
 65                  70                  75                  80

Leu Lys Glu

<210> SEQ ID NO 40
<211> LENGTH: 83
<212> TYPE: PRT
<213> ORGANISM: Artificial
<220> FEATURE:
<223> OTHER INFORMATION: N-terminal of Internalin protein

<400> SEQUENCE: 40

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
 50                  55                  60

Val Arg Tyr Leu Leu Leu Arg Ser Asn Lys Leu His Asp Ile Ser Ala
 65                  70                  75                  80

Leu Lys Glu

<210> SEQ ID NO 41
<211> LENGTH: 83
<212> TYPE: PRT
<213> ORGANISM: Artificial
<220> FEATURE:
<223> OTHER INFORMATION: N-terminal of Internalin protein

<400> SEQUENCE: 41

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
 50                  55                  60

Val Arg Met Leu Ile Leu Arg Ser Asn Lys Leu His Asp Ile Ser Ala
 65                  70                  75                  80

Leu Lys Glu

<210> SEQ ID NO 42
<211> LENGTH: 83
<212> TYPE: PRT
<213> ORGANISM: Artificial
<220> FEATURE:
<223> OTHER INFORMATION: N-terminal of Internalin protein

<400> SEQUENCE: 42

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
```

```
                    20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Val Leu Met Leu Arg Ser Asn Lys Leu His Asp Ile Ser Ala
65                  70                  75                  80

Leu Lys Glu

<210> SEQ ID NO 43
<211> LENGTH: 83
<212> TYPE: PRT
<213> ORGANISM: Artificial
<220> FEATURE:
<223> OTHER INFORMATION: N-terminal of Internalin protein

<400> SEQUENCE: 43

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Lys Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu

<210> SEQ ID NO 44
<211> LENGTH: 83
<212> TYPE: PRT
<213> ORGANISM: Artificial
<220> FEATURE:
<223> OTHER INFORMATION: N-terminal of Internalin protein

<400> SEQUENCE: 44

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Lys Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu

<210> SEQ ID NO 45
<211> LENGTH: 83
<212> TYPE: PRT
<213> ORGANISM: Artificial
<220> FEATURE:
<223> OTHER INFORMATION: N-terminal of Internalin protein

<400> SEQUENCE: 45

Glu Thr Ile Thr Val Ser Thr Pro Ile Lys Gln Ile Phe Pro Asp Asp
1               5                   10                  15
```

```
Ala Phe Ala Glu Thr Ile Lys Ala Asn Leu Lys Lys Lys Ser Val Thr
         20                  25                  30

Asp Ala Val Thr Gln Asn Glu Leu Asn Ser Ile Asp Gln Ile Ile Ala
         35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu

<210> SEQ ID NO 46
<211> LENGTH: 83
<212> TYPE: PRT
<213> ORGANISM: Artificial
<220> FEATURE:
<223> OTHER INFORMATION: N-terminal of Internalin protein

<400> SEQUENCE: 46

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
         20                  25                  30

Asp Ala Val Thr Gln Asn Glu Leu Asn Ser Ile Asp Gln Ile Ile Ala
         35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu

<210> SEQ ID NO 47
<211> LENGTH: 83
<212> TYPE: PRT
<213> ORGANISM: Artificial
<220> FEATURE:
<223> OTHER INFORMATION: N-terminal of Internalin protein

<400> SEQUENCE: 47

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
         20                  25                  30

Asp Ala Val Thr Gln Asn Glu Leu Asn Ser Ile Asp Gln Ile Ile Ala
         35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu

<210> SEQ ID NO 48
<211> LENGTH: 83
<212> TYPE: PRT
<213> ORGANISM: Artificial
<220> FEATURE:
<223> OTHER INFORMATION: N-terminal of Internalin protein

<400> SEQUENCE: 48
```

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Lys Ala
                35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu
```

<210> SEQ ID NO 49
<211> LENGTH: 83
<212> TYPE: PRT
<213> ORGANISM: Artificial
<220> FEATURE:
<223> OTHER INFORMATION: N-terminal of Internalin protein

<400> SEQUENCE: 49

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Lys Ala
                35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu
```

<210> SEQ ID NO 50
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 50

```
Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
            50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125
```

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 51
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 51

Leu Thr Asn Leu Thr Tyr Leu Thr Leu Glu Ser Asn Gln Leu Gln Ser
1               5                   10                  15

Leu Pro Asn Gly Val Phe Asp Lys Leu Thr Asn Leu Lys Glu Leu Gln
                20                  25                  30

Leu Trp Ala Asn Gln Leu Gln Ser Leu Pro Asp Gly Val Phe Asp Lys
            35                  40                  45

Leu Thr Asn Leu Thr Tyr Leu Asn Leu Ala Phe Asn Gln Leu Gln Ser
50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
                100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 52
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 52

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
                20                  25                  30

Leu Trp Ala Asn Gln Leu Gln Ser Leu Pro Asp Gly Val Phe Asp Lys
            35                  40                  45

```
Leu Thr Asn Leu Thr Tyr Leu Asn Leu Ala Phe Asn Gln Leu Gln Ser
 50                  55                  60

Leu Pro Lys Gly Val Phe Asp Lys Leu Thr Asn Leu Thr Glu Leu Asp
 65                  70                  75                  80

Leu Ser Tyr Asn Gln Leu Gln Ser Leu Pro Lys Gly Val Phe Asp Lys
                 85                  90                  95

Leu Thr Gln Leu Lys Asp Leu Arg Leu Tyr Gln Asn Gln Leu Lys Ser
                100                 105                 110

Val Pro Asp Gly Val Phe Asp Arg Leu Thr Ser Leu Gln Tyr Ile Trp
                115                 120                 125

Leu His Asp Asn Pro Trp Asp Cys Thr Cys Pro Gly Ile Arg Tyr Leu
130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
                180

<210> SEQ ID NO 53
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 53

Leu Thr Asn Leu Thr Tyr Leu Thr Leu Glu Pro Asn Gln Leu Gln Ser
 1               5                  10                  15

Leu Pro Asn Gly Val Phe Asp Lys Leu Thr Asn Leu Lys Glu Leu Gln
                 20                  25                  30

Leu Trp Ala Asn Gln Leu Gln Ser Leu Pro Asp Gly Val Phe Asp Lys
             35                  40                  45

Leu Thr Asn Leu Thr Tyr Leu Asn Leu Ala Phe Asn Gln Leu Gln Ser
 50                  55                  60

Leu Pro Lys Gly Val Phe Asp Lys Leu Thr Asn Leu Thr Glu Leu Asp
 65                  70                  75                  80

Leu Ser Tyr Asn Gln Leu Gln Ser Leu Pro Lys Gly Val Phe Asp Lys
                 85                  90                  95

Leu Thr Gln Leu Lys Asp Leu Arg Leu Tyr Gln Asn Gln Leu Lys Ser
                100                 105                 110

Val Pro Asp Gly Val Phe Asp Arg Leu Thr Ser Leu Gln Tyr Ile Trp
                115                 120                 125

Leu His Asp Asn Pro Trp Asp Cys Thr Cys Pro Gly Ile Arg Tyr Leu
130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
                180

<210> SEQ ID NO 54
<211> LENGTH: 183
<212> TYPE: PRT
<213> ORGANISM: Artificial
```

<220> FEATURE:
<223> OTHER INFORMATION: fused polypaptide of repeat module of VLR
    protein and C-terminal of VLR protein

<400> SEQUENCE: 54

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 55
<211> LENGTH: 183
<212> TYPE: PRT
<213> ORGANISM: Artificial
<220> FEATURE:
<223> OTHER INFORMATION: fused polypaptide of repeat module of VLR
    protein and C-terminal of VLR protein

<400> SEQUENCE: 55

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140

```
Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180
```

<210> SEQ ID NO 56
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 56

```
Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
                20                  25                  30

Leu Trp Ala Asn Gln Leu Gln Ser Leu Pro Asp Gly Val Phe Asp Lys
            35                  40                  45

Leu Thr Asn Leu Thr Tyr Leu Asn Leu Ala Phe Asn Gln Leu Gln Ser
        50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
                100                 105                 110

Val Pro Asp Gly Val Phe Asp Arg Leu Thr Ser Leu Gln Tyr Ile Trp
                115                 120                 125

Leu His Asp Asn Pro Trp Asp Cys Thr Cys Pro Gly Ile Arg Tyr Leu
            130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180
```

<210> SEQ ID NO 57
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 57

```
Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
                20                  25                  30

Leu Trp Ala Asn Gln Leu Gln Ser Leu Pro Asp Gly Val Phe Asp Lys
            35                  40                  45

Leu Thr Asn Leu Thr Tyr Leu Asn Leu Ala Phe Asn Gln Leu Gln Ser
        50                  55                  60
```

```
Leu Pro Lys Gly Val Phe Asp Lys Leu Thr Asn Leu Thr Glu Leu Asp
 65                  70                  75                  80

Leu Ser Tyr Asn Gln Leu Gln Ser Leu Pro Lys Gly Val Phe Asp Lys
                 85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 58
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 58

Leu Thr Asn Leu Thr Tyr Leu Thr Leu Glu Pro Asn Gln Leu Gln Ser
1               5                  10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
            35                  40                  45

Leu Thr Asn Leu Thr Tyr Leu Asn Leu Ala Phe Asn Gln Leu Gln Ser
        50                  55                  60

Leu Pro Lys Gly Val Phe Asp Lys Leu Thr Asn Leu Thr Glu Leu Asp
 65                  70                  75                  80

Leu Ser Tyr Asn Gln Leu Gln Ser Leu Pro Lys Gly Val Phe Asp Lys
                 85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 59
<211> LENGTH: 183
<212> TYPE: PRT
<213> ORGANISM: Artificial
<220> FEATURE:
<223> OTHER INFORMATION: fused polypaptide of repeat module of VLR
```

-continued protein and C-terminal of VLR protein

<400> SEQUENCE: 59

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 60
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 60

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly

```
                145                 150                 155                 160
Ser Val Ala Pro Asp Ser Ala Lys Cys Ser Gly Ser Gly Lys Pro Val
                    165                 170                 175

Arg Ser Ile Ile Cys Pro Thr
                180

<210> SEQ ID NO 61
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 61

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
                20                  25                  30

Leu Trp Ala Asn Gln Leu Gln Ser Leu Pro Val Gly Val Phe Asp Lys
            35                  40                  45

Leu Thr Asn Leu Thr Tyr Leu Asn Leu Ala Phe Asn Gln Leu Gln Ser
        50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
                100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
        130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
                180

<210> SEQ ID NO 62
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 62

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
                20                  25                  30

Leu Trp Ala Asn Gln Leu Gln Ser Leu Pro Asp Gly Val Phe Asp Lys
            35                  40                  45

Leu Thr Asn Leu Thr Tyr Leu Asn Leu Ala Phe Asn Gln Leu Gln Ser
        50                  55                  60

Leu Pro Lys Gly Val Phe Asp Lys Leu Thr Asn Leu Thr Glu Leu Asp
```

```
                 65                  70                  75                  80
Leu Ser Tyr Asn Gln Leu Gln Ser Leu Pro Lys Gly Val Phe Asp Lys
                 85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
        130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180
```

<210> SEQ ID NO 63
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 63

```
Leu Thr Asn Leu Thr Tyr Leu Thr Leu Glu Pro Asn Gln Leu Gln Ser
1               5                  10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
        130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180
```

<210> SEQ ID NO 64
<211> LENGTH: 183
<212> TYPE: PRT
<213> ORGANISM: Artificial

```
<220> FEATURE:
<223> OTHER INFORMATION: fused polypaptide of repeat module of VLR
      protein and C-terminal of VLR protein

<400> SEQUENCE: 64

Leu Thr Asn Leu Thr Tyr Leu Val Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 65
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 65

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Glu Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140
```

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
            165                 170                 175

Arg Ser Ile Ile Cys Pro Thr
            180

<210> SEQ ID NO 66
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 66

Leu Thr Asn Leu Thr Tyr Leu Thr Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Lys Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Glu Ile Trp
        115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
            165                 170                 175

Arg Ser Ile Ile Cys Pro Thr
            180

<210> SEQ ID NO 67
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 67

Leu Thr Asn Leu Thr Tyr Leu Val Leu Glu Pro Asn Gln Leu Gln Ser
1               5                   10                  15

Leu Pro Asn Gly Val Phe Asp Lys Leu Thr Asn Leu Lys Glu Leu Gln
            20                  25                  30

Leu Trp Ala Asn Gln Leu Gln Ser Leu Pro Asp Gly Val Phe Asp Lys
        35                  40                  45

Leu Thr Asn Leu Thr Tyr Leu Asn Leu Ala Phe Asn Gln Leu Gln Ser
    50                  55                  60

```
Leu Pro Lys Gly Val Phe Asp Lys Leu Thr Asn Leu Thr Glu Leu Asp
 65                  70                  75                  80

Leu Ser Tyr Asn Gln Leu Gln Ser Leu Pro Lys Gly Val Phe Asp Lys
                 85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
            130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 68
<211> LENGTH: 183
<212> TYPE: PRT
<213> ORGANISM: Artificial
<220> FEATURE:
<223> OTHER INFORMATION: fused polypaptide of repeat module of VLR
      protein and C-terminal of VLR protein

<400> SEQUENCE: 68

Leu Thr Asn Leu Thr Tyr Leu Thr Leu Glu Pro Asn Gln Leu Gln Ser
  1               5                  10                  15

Leu Pro Asn Gly Val Phe Asp Lys Leu Thr Asn Leu Lys Glu Leu Gln
                 20                  25                  30

Leu Trp Ala Asn Gln Leu Gln Ser Leu Pro Asp Gly Val Phe Asp Lys
             35                  40                  45

Leu Thr Asn Leu Thr Tyr Leu Asn Leu Ala Phe Asn Gln Leu Gln Ser
         50                  55                  60

Leu Pro Lys Gly Val Phe Asp Lys Leu Thr Asn Leu Thr Glu Leu Asp
 65                  70                  75                  80

Leu Ser Tyr Asn Gln Leu Gln Ser Leu Pro Lys Gly Val Phe Asp Lys
                 85                  90                  95

Leu Thr Gln Leu Lys Asp Leu Glu Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
            130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180
```